US012702864B2

(12) United States Patent
Nissenbaum et al.

(10) Patent No.: US 12,702,864 B2
(45) Date of Patent: Aug. 11, 2026

(54) INCREASED EFFECTIVENESS OF UV PATHOGEN ERADICATION

(71) Applicants: Israel Nissenbaum, Brooklyn, NY (US); Asher Baum, Brooklyn, NY (US); Mitchell J. Bogart, New Haven, CT (US)

(72) Inventors: Israel Nissenbaum, Brooklyn, NY (US); Asher Baum, Brooklyn, NY (US); Mitchell J. Bogart, New Haven, CT (US)

( * ) Notice: Subject to any disclaimer, the term of this patent is extended or adjusted under 35 U.S.C. 154(b) by 672 days.

(21) Appl. No.: 18/097,367

(22) Filed: Jan. 16, 2023

(65) Prior Publication Data

US 2023/0310882 A1 Oct. 5, 2023

Related U.S. Application Data

(63) Continuation-in-part of application No. 17/244,860, filed on Apr. 29, 2021, now Pat. No. 11,554,187.

(60) Provisional application No. 63/017,407, filed on Apr. 29, 2020, provisional application No. 63/044,641, filed on Jun. 26, 2020, provisional application No. 63/077,003, filed on Sep. 11, 2020, provisional (Continued)

(51) Int. Cl.

| | |
|---|---|
| ***A61L 2/00*** | (2006.01) |
| ***A61B 1/00*** | (2006.01) |
| ***A61N 1/00*** | (2006.01) |
| ***A61N 5/06*** | (2006.01) |
| ***A61N 5/067*** | (2006.01) |
| ***G01N 21/00*** | (2006.01) |

(52) U.S. Cl.

CPC ......... *A61N 5/0624* (2013.01); *A61N 5/0603* (2013.01); *A61N 5/067* (2021.08); *A61N 2005/0612* (2013.01); *A61N 2005/063* (2013.01); *A61N 2005/0642* (2013.01); *A61N 2005/0661* (2013.01)

(58) Field of Classification Search

CPC ........ A61B 90/70; A61M 1/3661; A61L 2/10; A61L 2/24; A61L 2/26; A61L 9/20

USPC .............. 422/24; 250/455.11, 454.11, 492.1; 600/15, 101

See application file for complete search history.

(56) References Cited

U.S. PATENT DOCUMENTS

2006/0264919 A1* 11/2006 Schaaf ............... A61B 1/00142 600/101
2017/0182194 A1* 6/2017 Shin ....................... A61B 90/70
2019/0168023 A1* 6/2019 Eltorai ................ A61M 1/3661

* cited by examiner

*Primary Examiner* — Monzer R Chorbaji

(74) *Attorney, Agent, or Firm* — Israel Nissenbaum; Yitzy Nissenbaum

(57) ABSTRACT

Manual, automated and mass methods and devices, for enhancing the effect of UV light disinfection (at UV wavelength of 200 nm to 340 nm) of transmitted UV light on or in humans and devices by at least one of the steps of: a) increasing controllable output power of a UV emitting device, including using high power UV lasers or direct placement of UV light sources, b) increasing the efficiency of UV disinfection effect with the placement of the UV emitting device including by use of side emitting fibers with uniform output and distant placement directed at surgical sites, otoscope type handheld devices directing UV light into infected orifices, biofilm disruption, fluorescent marking of pathogens and c) providing protocols for various enhanced pathogen eradication applications including tissue clearing to increase depth of penetration, use of aspiration needles for (Continued)

access to pathogens, site disinfection to increase cancer remission and implant in situ disinfection.

9 Claims, 21 Drawing Sheets

Related U.S. Application Data application No. 63/118,638, filed on Nov. 25, 2020, provisional application No. 63/139,294, filed on Jan. 19, 2021, provisional application No. 63/149,611, filed on Feb. 15, 2021.

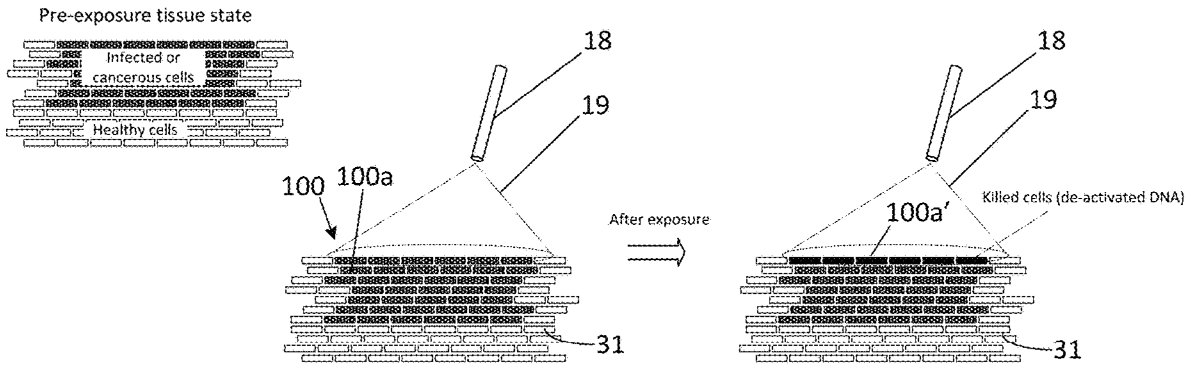

Step 1 – Practitioner delivers an initial fully effective amount of power to the surface area to be irradiated (Normal Medium power).

Fig 5A

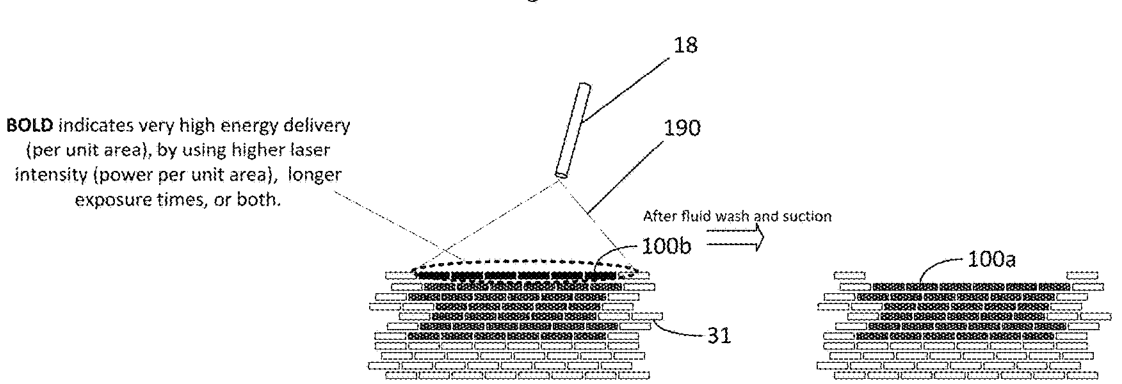

Step 2 – Practitioner ablates the deactivated and killed layer of cancer cells by using higher power exposures of UV-C to kill, soften, and have washed away the layer of killed cells. (High power).

Fig 5B

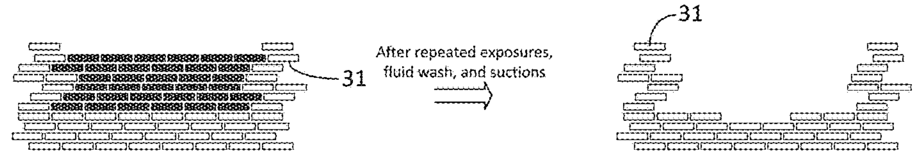

Step 3 – Practitioner repeats steps 1&2 repeatedly, delivering a lower amount of power to the surface area to be irradiated to disrupt The RNA/ DNA of exposed cancer cells. Then high power flush and suction.

Fig 5C

Surgical site – photo without fluorescence

Surgical site - fluorescing Pseudomonas aeruginosa bacteria from 405nm light

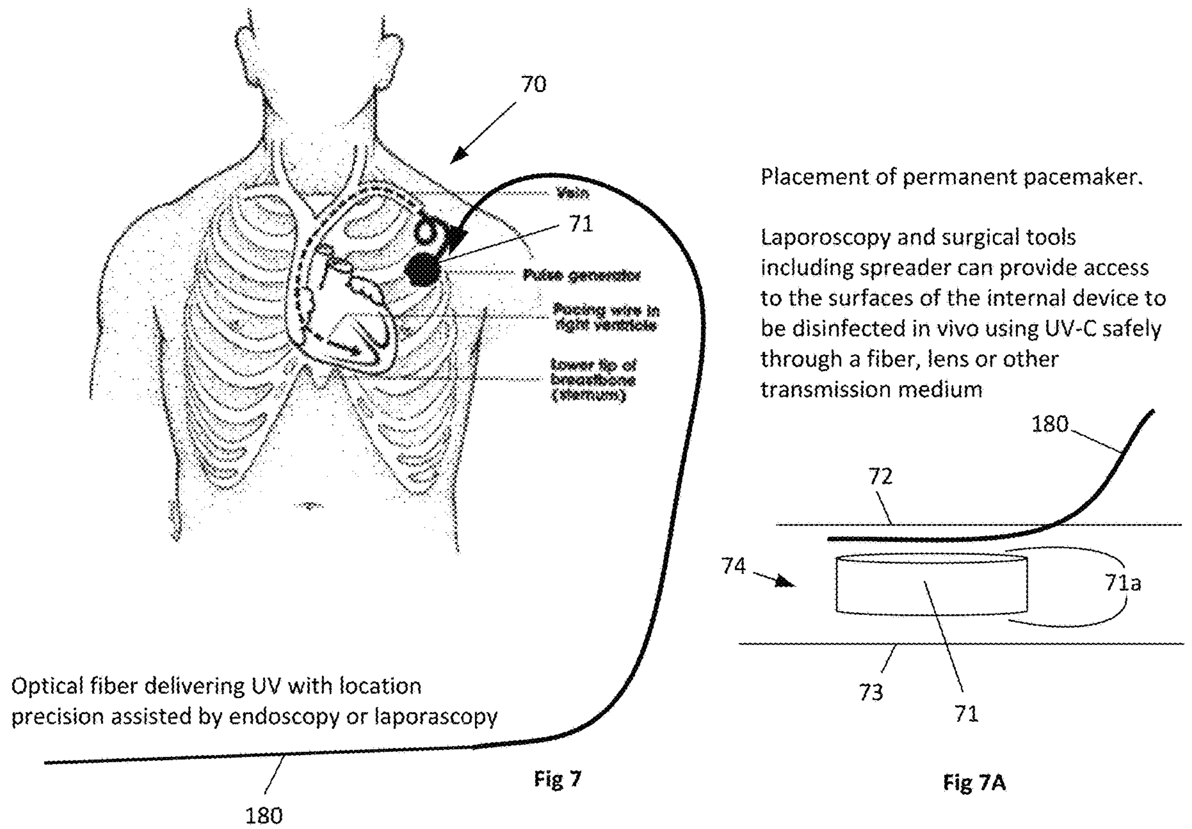
Fig 7
Fig 7A
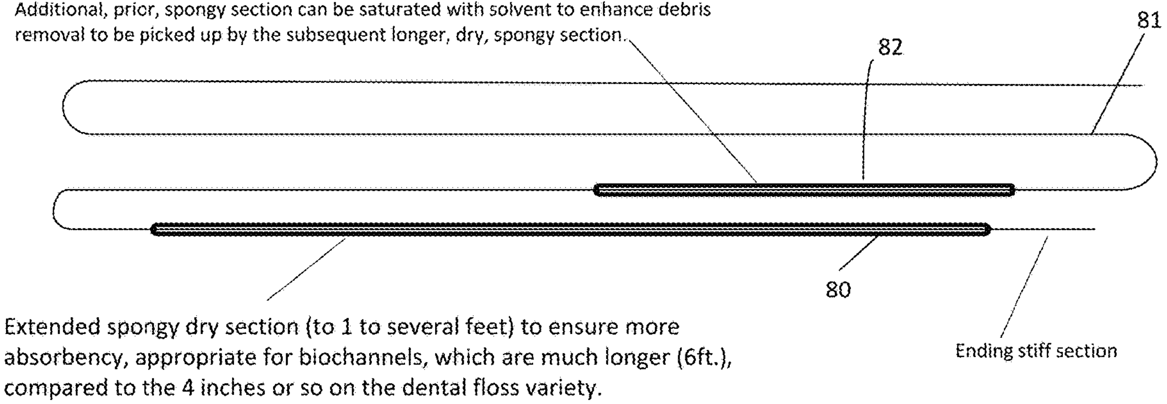
Fig 8

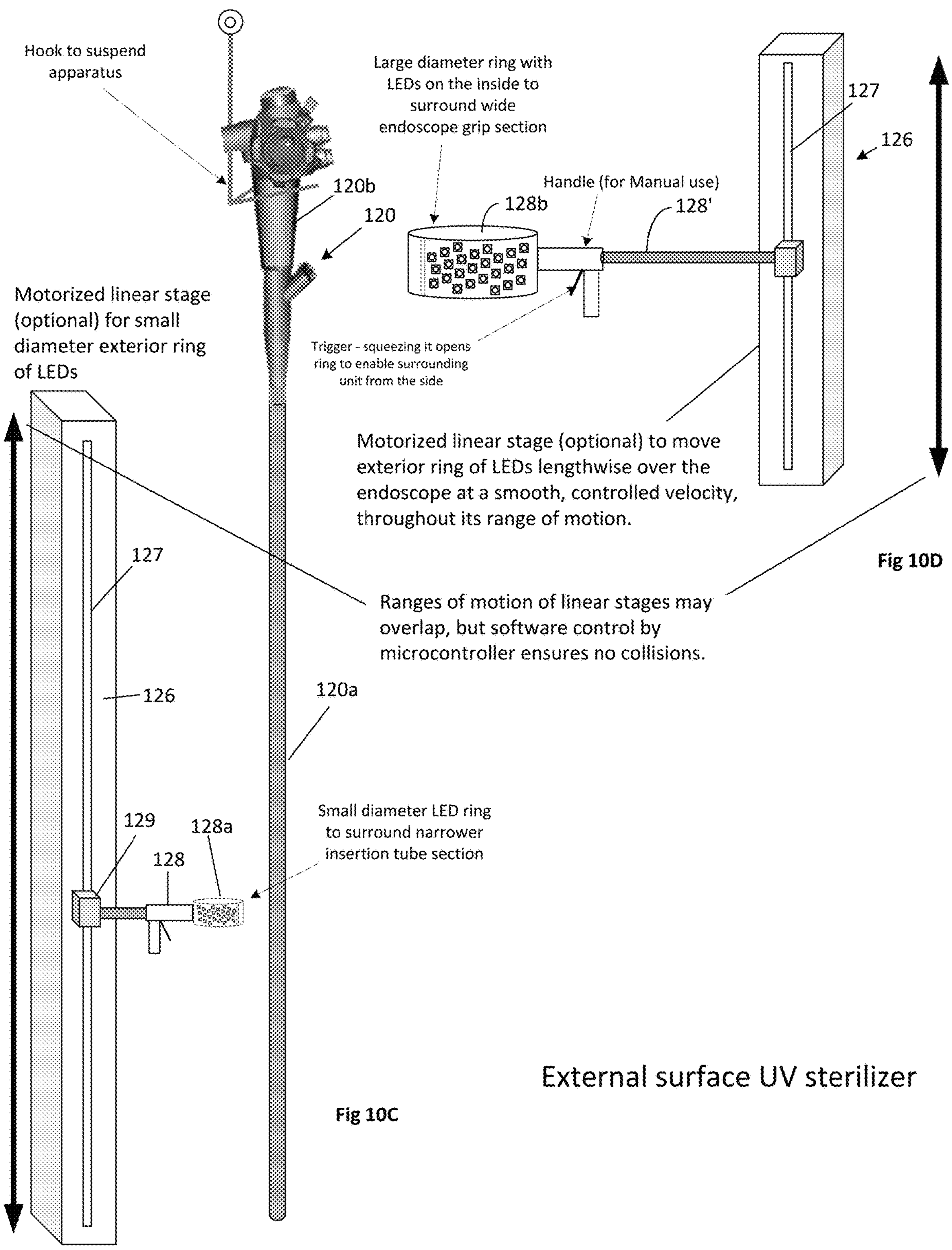
Hook to suspend apparatus
Large diameter ring with LEDs on the inside to surround wide endoscope grip section
127
126
120b
120
Handle (for Manual use)
128b
128'
Motorized linear stage (optional) for small diameter exterior ring of LEDs
Trigger - squeezing it opens ring to enable surrounding unit from the side
Motorized linear stage (optional) to move exterior ring of LEDs lengthwise over the endoscope at a smooth, controlled velocity, throughout its range of motion.
Fig 10D
127
Ranges of motion of linear stages may overlap, but software control by microcontroller ensures no collisions.
126
120a
129
128a
128
Small diameter LED ring to surround narrower insertion tube section
External surface UV sterilizer
Fig 10C

INCREASED EFFECTIVENESS OF UV PATHOGEN ERADICATION

This application is a continuation-in-part of US patent application Ser. No. 17/244,860, filed Apr. 29, 2021, now U.S. Pat. No. 11,554,187, issued Jan. 17, 2023, which in turn takes priority from provisional patent applications: 63/017,407, filed Apr. 29, 2020; 63/044,641, filed Jun. 26, 2020; 63/077,003, filed Sep. 11, 2020; 63/118,638, filed Nov. 25, 2020; 63/139,294, filed Jan. 19, 2021; and 63/149,611, filed Feb. 15, 2021, the disclosures of which are incorporated herein by reference thereto.

FIELD OF THE INVENTION

This invention relates to methods and devices for the enhancement of pathogen eradication with UV light primarily by remote means and particularly relates to the eradication of pathogens by UV light in or on medical instruments and to the non-traumatic eradication, by UV light, of pathogens within or on human or animal bodies.

BACKGROUND

In said parent patent applications, devices and methods were disclosed which effectively eradicated pathogens such as viruses, bacteria and cancer (defined as a pathogen), primarily by means of remote application of UV light. Such UV light was specifically exemplified as coming from an LED UV light source (though other light sources were described), to infected areas such as in biopsy channels of endoscopes and within a human body by means of a transmission medium, in particular, with an embodiment of a fiber optic transmission medium. The specific pathway of the eradication was by means of a disruption of DNA/RNA of the pathogens (or cancer cells) on a molecular level without or with minimal physical trauma to the organ or healthy cells harboring the cancer, with a complete or almost complete elimination of pathogens or a significant reduction of pathogen presence sufficient to alleviate untoward conditions. Such eradication effectiveness was however constrained, in efficient utilization, by considerations, such as application time and power of applied UV light, lack of effective feedback, skill required for application, and limitations encountered with minimized depth of penetration of UV light. In further discussions hereafter, the term "pathogen", as used herein, is defined as referring to noxious and/or toxic elements having DNA/RNA, subject to disruption, and specifically refers to viruses, bacteria, cancer (though not technically a pathogen but being toxic and having DNA/RNA), mold and mildew, and other micro-organisms. Also included in the term "pathogen", for purposes of the invention disclosed herein, are cells and tissues which are healthy in themselves but are excessive, with such excess, providing noxious conditions. In addition, healthy cells which are presently benign, but which may become toxic, such as by being adjacent to non-healthy cells such as cancer cells or viruses and bacteria, which may spread, are similarly defined herein as being "pathogens" or "pathogenic" for purposes of being disrupted with UV light. The term "eradication", as used herein, refers to the deactivation of noxious and/or toxic elements by disruption of DNA/RNA contained in these elements with breakage of the bonds of the helix structure of the DNA/RNA components. The terms "disinfection", "sanitization" and "sterilization", as used herein, are used interchangeably as referring to a medically acceptable cleaning. The term "sterilization", when so indicated, is an FDA recognized term for total or log 6 or greater reduction of pathogens.

The terms "transmission" and "transmission media (medium)" of and with UV light, as used herein, and as used in the parent application, refer to the acting as a vehicle to transport a sufficiently acceptable power-output of UV inactivating energy to a pathogenic, or possibly pathogenic, site, including viruses, bacteria, cancer and other known or otherwise defined pathogens. The terms include fiber optics, liquid light guides, light pipes, and optical lenses and lens systems specifically configured to provide a focal length distance which acts similarly to a fiber in transmitting disruptive UV light from a UV light-source via collimating (with essentially parallel light rays), focusing or other lens, lens combination, or lens and fiber combination, and transports the light along its focal length to be directed to the pathogen site. This is in contrast to simple transparent media, such as glass or clear plastic panes, as protectively used such as in flashlights which simply allow a light pass-through. The term "angle of acceptance" is used generically with respect to all transmission media and refers to the angle or direction for light and particularly UV light of a designated wavelength to be successfully introduced into the transmission media for the transmission thereof. "Energy" (Power×time) and "power (Energy/time)" are used interchangeably herein. The term "focusing" in this, and the parent application, has the meaning, depending on context, of technical optical control with a lens or the like, or a generic meaning of directing transmitted light into small areas. The term "reasonable period of time" which is used with a period of UV light pathogen eradication is a function of the particular application of the pathogen eradication, the reasonable economic or medical exigencies and severity of pathogen infection. Thus, disinfection of non-biological devices such as endoscopes may be longer (depending on requisite processing requirements) than required for invasive medical procedures. Reasonable time for medical procedures such as cancer treatment may be longer than for virus or bacteria treatment. In general, without specific limitation, reasonable time should not normally exceed a half hour for each pathogen eradication site. Unless otherwise indicated, the term "site", as used herein, refers to a single pathogenic or suspected pathogenic area exposed to UV light. The term "full", as used herein, is to be construed as being "substantially full" unless otherwise indicated.

SUMMARY

In view of the above, it is an object to provide methods and devices for enhancing the effect of UV light disinfection (at UV wavelength of from 200 nm to 340 nm and most particularly in the UV-C range of 250 nm to 285 nm, with a peak effectiveness for DNA disruption at about 265 nm and 220 nm being considered safe for surface use only, but with essentially no depth of penetration) and pathogen eradication by at least one of the steps of (among others): a) increasing controllable output power of a UV emitting device, b) increasing the efficiency of UV disinfection effect with the placement of the UV emitting device and c) providing protocols for various enhanced pathogen eradication applications.

It is a further object to provide such controlled increased power with a laser UV light source, having controlled characteristics, to within the DNA/RNA disruption UV wavelength (most particularly centered at 266 nm though other wave lengths within the UV-C range such as 261 nm are available and useful) and power range, for eradicating pathogens, before onset of traumatic ablation or surgical transection of tissue and to optionally use minimal ablation levels for removal of dead pathogens or cancer cells, with at least some diffusion-of-light expedients. Though lasers with UV transmission media are known, they have not, as far as is known, been generally used for disinfection and have been configured and utilized for ablative purposes such as surgical transection or for spectroscopic analysis.

It is another object to utilize controlled, increased power of a UV laser light, and of very high-powered UV LEDs or similar high power light sources, in conjunction with a side-emitting optical fiber with a gradient of light output and substantially unform power output along its side. Side emitting fibers coupled to UV LED power such as disclosed in US Patent Publication 2021/0122667 have shown killing of pathogens. However, this publication discloses a relatively low power LED UV light source with a microwatt output requiring well in excess of 30 minutes for pathogen eradication and with only about 8 inches of side emission pathogen killing power—decreasing with distance from the UV light source). This is a very inconsistent unpredictable output rendering it difficult to provide effective pathogen disinfection in reasonably predictive times. However, with the vastly increased UV output power, a full-length fiber (typically 500-600 mm in the biopsy channel of a bronchoscope) or one of another appropriate length, can be made to be effectively suitable for full insertion into the biopsy channel of an endoscope with uniform power outputs in the multiple milliwatt range. Emission of UV light from proximal to distal end thereof is sufficient to rapidly kill pathogens in its exposure area with resultant full channel disinfection and greater predictability in pathogen eradication effect. With modification, as described hereinafter, an entire side emitting fiber may be made with an essentially uniform UV light side emitting output at relatively high pathogen killing power.

It is a still further object to increase the efficiency of UV emitting devices, by utilizing a lens transmission medium for relatively short-range UV light transmission particularly collimated transmission (or with optical transmission focusing or a combination of collimation and focusing) with pathogen disruption in partially accessible human or animal body areas such as in or adjacent to respiratory, alimentary or excretory orifices. Alternatively, the collimated (and/or focused) UV light pathogen disruption may be utilized in surgical procedures with body incisions and for protection against common pathogens such as MRSA (particularly during surgical procedures), and SSIs which are difficult to remove, even with antibiotics or common sterilization expedients. UV light, because of its DNA/RNA disruption is effective against any pathogen containing DNA/RNA including the ones resistant to other inactivation and sterilization methods.

It is an object to provide non-intrusive bathing of surgical sites before, during and after surgical procedures, with directed and pathogenic clearing UV light, to maintain an acceptably sterile surgical site with prevention of MRSA staph infections and possible sources of sepsis, not readily eliminated by normal disinfection procedures.

In another object surgical sites may also be optionally bathed with selected other wavelength lights, with known parameters and procedures, to cause bacteria to fluoresce and be more easily and effectively targeted in real time in situ situations. Since collimated light maintains power over the length of the collimation, UV light from a source may be positioned at a distance (such as out of the way of a surgical procedure) while maintaining pathogen killing effectiveness.

It is yet another object to provide pathogen treatment protocols for enhanced pathogen eradication such as by including successive DNA/RNA disruption eradication of surface pathogens, followed by ablative removal of dead cells and tissues, to increase effective UV light penetration and reach, to underlying tissue.

In another object, depth of penetration limitations are also sidestepped with protocols involving surface treatments which facilitate prevention of surface pathogen spreading. Internal reaming formation and widening of access lumens is similarly possible with aspiration needle carriers of UV light transmission members. With access lumens being formed, expedients such as suction and/or washing may be viable for removal of dead cells. Dead cell removal may also be carried out by scavenging phagocytes but, while useful, this expedient may be constrained by long effective times. Robotic or automatic repetitive operations according to a pre-mapped operational route is more effective with respect to properly blanketing DNA/RNA disruption sites.

Another object for increasing enhanced pathogen eradication is by rendering the pathogen site, such as cancer tissue or tumor site itself, more permeable to light penetration by means of known tissue clearing procedures particularly such as by removal of light blocking pigments and light scattering lipids with selected solvents to increase transparency of the tissue, with resultant greater UV light penetration depth and particularly by in vivo procedures.

It is still yet another object to provide protocols and structures for UV light to effectively disinfect surfaces of implants and implant leads in situ within a body without the need for surgical removal of the implants or their leads.

It is another object to provide pathogen treatment protocols for increasing the extent of cancer remission by surface UV treatment of excised cancer sites especially as part of a surgical procedure, and similarly useful in periodic treatments subsequent to surgery as well.

As another object, under appropriate conditions, for increasing power output, one or more UV LEDs or other small UV light sources may be directly positioned, within a sufficiently large volume of an insertion device, such as a catheter or biopsy channel of an endoscope. The movably contained small UV light sources such as UV LEDs are properly oriented for direct UV light impingement, on pathogens within the insertion device without the need for attenuating transmission media and with increased UV light power.

Another object for increasing efficient use of transmitted UV light is with automated and with computer generated data which includes initial determination of actual available UV light power by means such as with power integrating measuring elements (integrated with or separated from the UV light source).

In this respect, available UV power level determination is coupled with controlled minimum and maximum dosage level determinations based on application distance, type of pathogen, power levels and DNA/RNA disruption efficiency to provide an automatic repeatable level of effective UV light energy delivered. A study and presentation of the effect of deep LUV light on pathogens by the IEEE of Tech Talk Semiconductors Optoelectronics on 16 Apr. 2020, entitled *Ultraviolet-LED Maker Demonstrates* 30 *Second Coronavirus Kill* presented by Seoul Viosys and authored by Samuel K. Moore, provides a rough basis for determining the parameters of UV light (wave-length, application distance, applied power and duration) needed to have a disruptive effect on pathogens. The study provided the results of the direct (not transmitted) output of a non-optimal 275 nm LED on viral cells (coronavirus) with the conclusion that the virus was effectively killed in 30 seconds, with an output power of about 20 mW (thus an energy of 600 mJ) at a distance of 3 cm and an output beam angle of 120°. As a result of the inverse square rule, closer distances dramatically increase effective applied power. In the parent application, extensive prior art tables were cited with detailed descriptions of hundreds of virus and bacteria pathogens with the required amounts of UV light treatment for the eradication thereof. These and other tables may be used in determinations, whether manual or automatic to determine the requisite parameters for specific pathogen eradication on an ad hoc basis.

A still further object, with respect to non-biological disinfection applications, for increasing efficiency and reliability in utilizing UV light for pathogen eradication is by including controlled and timed UV surface application onto pathogen infected areas (or suspected infected areas) and preparatory treatments to enhance UV light impingement on pathogen infected surfaces, particularly with biofilm disruption.

A further object for increasing efficiency of UV light utilization is the providing of a feedback determination loop wherein appropriate UV light application for pathogen eradication is controlled by real time feedback of extent of pathogen eradication, as a function of degree of pathogen infections needing disinfection.

Yet another object for efficient UV light efficiency entails the automating of disinfection of pathogen infected surfaces with controlled movement of a UV light source along the surface at effectively determined rates, and controlled power level application and distance between light source and pathogens.

Another object is to utilize small diameter aspiration needles to carry UV light fibers to nearly any part of a human body in vivo to provide LV light disinfection treatment thereto and to provide requisite preparatory materials such as for tissue clearing to such part.

Still another object for efficiently disinfecting items with en masse procedures is that of large scale automated sterilization of devices such as pipettes, hypodermics and the like which must be used in medically sterile condition.

Embodiments of methods herein for enhancing the pathogenic eradication effect of UV light of a wavelength between 200 nm to 340 nm on a pathogen infected area, include methods comprising at least one of the following steps.

a. The controllable output power of a UV light source emitting device is increased and directed within a difficult to access pathogenic containing area. Either direct placement of the UV light source or directed transmission of UV light from the UV light source is provided into the difficult to access area The direct or transmitted light maintains sufficient power to substantially eradicate pathogens in the pathogenic containing area, with DNA/RNA disruption.
b. UV light is trained, with directed transmission, onto a surgical site before, during and optionally after a surgical procedure to maintain a substantially pathogen free environment during the surgical procedure. In another embodiment, UV light is directed and transmitted through and onto an infected orifice for the disinfection thereof.
c. To increase depth of penetration of UV light, the pathogenic infected site is made susceptible to significant UV light penetration with pathogen eradication thereof by;
    i. rendering the pathogenic site more transmissive to UV light penetration;
    alternatively, a pathogenic infected site is isolated from non-infected sites, by:
    ii. utilizing UV light, pathogen eradication to form a pathogen eradicated barrier between the pathogen infected site and a non-pathogen infected site; or
    iii. rendering the pathogen infected site more susceptible to the significant UV light penetration with the repeated steps of pathogenic eradication of infected areas and removal of the pathogenic eradicated areas to expose additional pathogenic infected sites to the UV light.

Increasing UV Applied Output Power:

Generally, the invention, in one embodiment, comprises the increase of input and output UV light power, particularly of UV-C light from the generally low single and double digit milliwatt output power practically available from readily available UV LED light sources to triple digit milliwatts and higher output UV light power by means of lasers emitting light in the UV spectrum range. Lasers currently exist in the UV range of 266 nm and with output powers exceeding 1 watt. Such lasers are exceedingly expensive and are used primarily for high powered ablation purposes and in some cases for use in tissue transection, as a function of the available power. These lasers have been effectively coupled to optical fibers, primarily for control in precisely placing output laser light in effecting ablation or transection cutting purposes, particularly for corneal reshaping and eye surgery. Because of their inherent collimating characteristics and small beam diameter, they have never been considered, constructed or configured for disinfection purposes where broad areas are needed for any useful or effective disinfection. Accordingly, broad and scattered lighting sources such as LEDs and lamps have been exclusively utilized for such purpose. In the present application, the laser light characteristics of minimal beam diameter are required for proper coupling with transmission media such as optical fibers through an angle of acceptance to maintain power, but output from the transmission media is specifically spread out, widened, or diffused for increased contact with pathogens for effective widespread disruption.

A power output in the range of about 100 mW-200 mW, is believed to be a reasonable transition level between the traumatic destructive ablation and transection levels of a 266 nm laser and the lower levels of non-traumatic, molecular level UV-C DNA/RNA disruption, though The transition range may vary in accordance with LV light source parameters and pathogenic area properties.

Various parameters of laser light characteristics are involved in the appropriate transmission coupling of laser light with optical fibers. These include $M^2$ determination of beam quality (usually with values less than 1.5 being more useful for coupling efficiency) and beam diameter relative to fiber diameter and destructive heat considerations with high peak power lasers endemic with pulse lasers. Furthermore, good $M^2$ beam quality helps to allow more usable light to enter into the optical fiber, without having to further increase the peak power to maintain a desired output power through the optical fiber that needs to enter the fiber core.

A UV laser design configuration embodiment, with coupled fiber (or other transmission medium) should include expedients, if needed, to minimize effect of high generated heat due to prolonged or even short use of the coupled fiber. Continuous wave UV lasers, with minimized heat build-up, are a desired laser system for consistent and stable power outputs, however such laser are presently generally of higher cost, size, weight and bulk, and overall lower output powers.

The optical fibers used with the lasers may be specially treated to avoid burn-out, particularly if used with pulsed lasers of momentary high power pulses. Side emitting fibers normally are not effectively usable for disinfecting medical device channels such as biopsy channels. Such fibers have been disclosed (such as in the above cited publication) as being used with relatively low power LEDs with very low power output in the microwatt region, requiring exceedingly long exposure time (minimum of a half hour and usually up to several hours). In addition, the power output along the sides of such fibers have varying power intensities which rapidly drop with distance from the power source, such that fibers of more than about 8 inches (about 200 mm) have little or no power output at the distal end, whereas endoscope biopsy channels generally have much greater lengths (e.g., 500 mm-600 mm for bronchoscopes) and such fibers cannot effectively reach and sanitize the full length of endoscopes. The higher power enables even the distal end of a side emitting UV transmitting optical fiber, to be effectively sufficiently long to access the full length of a biopsy channel, to emit sufficient output power to eradicate pathogens in a more reasonable period of time.

It is also possible, with high power UV light sources such as the UV lasers, mentioned above, as well as UV LEDs with high power output and die size/fiber connection compatibility (and the like), to correct for the uneven UV light output of side-emitting fibers of the prior art and progressive exponential loss over distance. In a procedure similar to that known in the printing art, wherein black ink microdots are printed, laser formed microdots with light permeating holes, are formed herein in the cladding to a depth of the fiber core. These microdot holes are produced, with cladding transparency, at each point along the length of a clad fiber to control degree of UV light output and power. More microdot holes are formed at the distal end of the fiber as compared to the proximal end, with a gradient of concentration of microdots decreasing toward the proximal end. As a result, with this configuration and sufficient UV power, the final light transmitted at the end of the fiber is configured to provide a compensating transparency gradient whereby light, which is side-emitted through the laser microdot holes, has a reverse power output change, i.e., light output power at the fiber end close to the light source has the least power emission with the emission percentage increasing with distance from the light source. Thus, the strongest light emission percentage is at the most distant end of the fiber furthest from the power source and the weakest light emission percentage is at the proximal end of the fiber closest to the UV light source. With judicious arrangement, power output along each side portion may thereby be rendered substantially uniform or with predictable utilizable power outputs.

This re-ordering of light output power may be used to compensate for the otherwise increasing attenuation at the most distant end. With this arrangement, the entire length of the optical fiber may be made to have substantially uniform side-emission along its entire length. Though this entails loss of the fiber having the maximum possible absolute side-emission, it is otherwise advantageous such that the fiber can, for example, simply be placed within a pathogen infected area such as a biopsy channel and remain stationary without the need for longitudinal movement. The higher power UV laser light compensates for the areas shielded from side emission, to provide a useful and uniform (or predictable) side emitted light output power. This eliminates or minimizes fiber moving procedures such as timed fiber withdrawals or insertions with attendant dwell time uncertainties, as well as likely errors with manual manipulation. To compensate for loss of fiber core protection with the array of microdot addition of a protective polymeric UV-transmissive outer layer may be used to surround the fiber having microdot holes.

In another embodiment, in non-biological areas such as in the instrument or biopsy channel of an endoscope (such as a 4 mm diameter colonoscope) of areal cross sectional area in excess of about 12 mm2, output power may be increased by elimination of losses inherent with light collection and transmission, and UV LEDs of slightly smaller cross section dimensions (generally of lower power outputs) can be directly inserted into such areas, with full LED power (not attenuated by connection to a transmission medium) being available for direct pathogen eradication. Though the effectively smaller LEDs, suitable for direct insertion, are generally of lower power output, elimination of large transmission losses with the direct insertion with lower power UV LEDs, more than compensates for high power LEDs having large transmission power losses. UV LEDs on controller PC boards have been miniaturized to an extent wherein the diagonal dimensions of the UV LED with PC board is under 3 mm. They are accordingly directly placeable into larger instrument channels of endoscopes such as colonoscopes with large diameter instrument channels generally of 4 mm or larger. The LEDs in such configuration are most effectively arranged along the length of the channel with UV light being directed against the channel walls. A triangular configuration of three UV LEDs arranged to alternatively face the channel walls with a 120° angle of light emission serves to provide a full 360° angle coverage of the channel walls, for a complete disinfection. These arrangements are only exemplary, with varying number of LEDs and placements being possible, depending on available areas and volumes.

In a further area, of an embodiment with effectively higher UV output power, a transmission medium of an optical lens is utilizable in UV light application devices such as of otoscope type hand-held configuration which remotely directs collimated UV light over short distances directly into orifices such as nostrils or the mouth and throat, or in excretory areas even when positioned external to the orifice. Alternatively, incisions can provide access to internal sites within the body requiring disinfection. Transmission of light with collimating lenses is of higher efficiency with less transmission loss and more effective UV light power output. With such directed high UV power devices, surgery sites, including the patient and any surgical incision sites themselves may be safely and comprehensively sanitized from even the most difficult to remove MRSA staph pathogens with a quick site sanitization before, during and after surgery. The collimated UV light is directed from outside of the immediate surgical area, without interfering with the surgery, with light directed only at the immediate surgical area where operating personnel are wearing protective gloves and wherein directed UV light does not stray into unprotected areas. Disinfecting UV-C light normally has little depth of penetration and is a safe yet highly effective surface disinfection treatment against surface pathogens such as staph infection, MRSA and other SSIs. Incidence of sepsis is thereby readily reduced. Collimated light, in contrast to optically focused light, maintains a substantially constant intensity output of power/unit area over the distance of collimation, thereby effectively increasing the distance at which the light source may be positioned, without significant loss of delivered power.

Increasing UV Light Application Effect:

A further embodiment for increasing penetration depth involves the rendering of the pathogen site such as cancer tissue or tumor more transparent such as with the in vivo in situ removal of lipids and or pigments within the pathogen containing tissue by use of known methods such as with suitable solvents and detergents in controlled amounts to prevent or minimize side effects. An example of a process of in vivo tissue optical clearing is described in iScience entitled "*Physical and Chemical mechanisms of tissue optical clearing*", Volume 24, Issue 3, 19 Mar. 2021, 102178. Optical tissue clearing, particularly for in vivo purposes is an ongoing field of study with many improved, more efficient, faster and reduced side effect methods and materials being constantly developed for biological observation purposes.

In the described process, methyl benzoate (MBe) approved by the US FDA (21 CFR 172.515; FDA 2015) and the European Union (EU Regulation 1334/2008 & 178/2002; EU 2015) for use as a food-grade flavor ingredient and methyl salicylate (another food flavoring agent) are described as among chemicals which help render tissues substantially transparent. These compounds are non-toxic, or very mildly toxic, especially in small amounts, and they are used currently in foods, beverages and topical applications.

Though transparent rendering of tissues including tumors have generally been effected in dead animal specimens, this has been primarily done for examination of the specimens with instruments such as microscopes. Transparent renderings of tissues (tissue clearing) have recently been conducted in in vivo studies such as the above cited one, with minimal toxic effect, for the purpose of rendering animal (particularly mice) skin transparent, enabling direct viewing of ongoing biological processes. Use of an aspiration needle with controlled solvents and/other tissue clearing chemicals (determined with tumor or cancer site volume mapping) to minimally target only a tumor site (and some peripheral cells or tissue) with pigment or lipid removal solvents or detergents is of minimal concern because of the limited amount of the introduced solvents. Also, the generally minimal or non-toxic nature of the solvents and the fact that the tumor site is to be excised, in any event, further minimizes any safety concerns. It is further noted that the transparent effect may be only transitory with replenished lipids and pigments being formed in the cleared site.

As the pathogen site becomes more transparent (tissue inherently does not absorb light waves) the optical transmission depth of the DNA/RNA disrupting UV light becomes significantly enhanced. Pathogen disruption removal in conjunction with phagocytes and/or ablation procedures is more fully expedited. The increased transparency, in conjunction with greater applied UV power, can enable full pathogen sites such as cancer tumors to be effectively removed without surgery or common current highly traumatic and disruptive radiation such as X-rays and gamma rays, with minimal side effects and significantly less trauma. The UV fiber-containing needle can be inserted into the cleared tissue with radiation of UV light dependent on the end treatment of the fiber. Thus, a fiber with a full diffuser tip has a circular radiation and a depth of penetration on each side of the fiber in a 360° range. The needle moves the diffuser tip through the depth of the tumor whereby at least a substantial portion of a tumor can become bathed with pathogenic killing UV light. With a transparent tissue clearance allowing for fuller depth of penetration, the needle with fiber can be effectively used at a surface of the tumor and moved to various sites of the surface to insure fuller UV coverage of the entire tumor or cancer cell site. Substantially full side emitting fibers can further enhance the extent of pathogen eradicating UV light coverage.

It should be understood that current procedures for rendering tissues transparent require time, which may be several hours or days, and the procedure may be considered as a pre-op one, requiring return for the actual UV light treatment during a time window of maximum transparency. An article in Advanced Drug Delivery Reviews, volume 180, January 2022, 114037 validates the in vivo tissue clearing for introduction of treatments and viewing of results, with the describing of tumor tissue clearing for introduction of infrared radiation and heat therein for the treatment thereof.

Various protocols are included in embodiments of effective treatment, even without transparency pre-treatments, to enhance overall pathogen eradication despite lack of depth of penetration of typical UV light (generally on the order of about 40 microns).

A first protocol embodiment comprises the surface treatment by UV light of tumor removal sites such as the interior surface of a bladder. The effect of such surface treatment, especially if conducted over periodic times as determined by the specific type of cancer and/or aggressiveness, is the prevention or retardation of aggressive cancer from recurring in the original tumor or surrounding sites. This, in effect, serves to lengthen remission times without any surgical intervention, or in conjunction with known remission control procedures or surgical interventions. Specific examples of such surface treatments include inner bladder wall treatments, currently treated with BCG (weakened or killed tuberculosis bacteria) to provide a similar prophylactic treatment.

A second protocol embodiment comprises the formation of a perimeter including the reduction or elimination of blood channels with nutrient supplies at the interface of existing cancer cells and healthy cells to substantially retard metastization of the cancer cells into healthy cells. The UV light is directed at the surface of the interface and below it to a predetermined effective level by means of penetrating hollow needles such as aspiration needles commonly used for taking biopsy samples exemplified by EBUS and EUS needles containing the UV transmitting fiber or transmitting medium.

A third protocol includes multiple insertions in a closely-spaced geometry of light emitting aspiration needles with UV fiber transmitters to provide a widening area of a cored lumen amenable to inner surface UV light treatment with successive removal of dead cells by either phagocytes or physical ablation with suction or washing.

Implant Disinfection:

In situ direct disinfection of surgically implanted medical devices, including pacemakers, medication dispensing implants or other electrical devices, prosthetic devices such as hip and knee replacements, and rods or other structural devices, is effected, in another embodiment, with minimal surgical intervention. Surgical removal for disinfection procedures and reimplanting can be obviated (with reduced surgical side effects and expense) with the in situ application of UV light onto the surface of the implanted medical device on its surface and at its interface with cell tissue. Some medical devices, such as pacemakers and medicine dispensing devices are implanted in pockets between a patient's outer skin and underlying muscle such as in the left shoulder area of a patient just beneath the skin. In a disinfection procedure, an access incision for laparoscopic (as a non-limiting example of a guiding insertion device) insertion of the UV carrying fiber is made, proximate to the implant. The UV fiber is inserted between the implant and the holding pocket to effect disinfection by applied UV light. In various embodiments, multiple insertions may be required. Configuration of the fiber end may be modified to provide a limited radial UV light output in just the direction of the implant. With the fiber being inserted directly through a skin incision, the fiber end may also be provided with a rigid transparent, extending or extended, surface-prying blade which serves the purpose of prying skin from implant, thereby facilitating insertion of the fiber end between pocket walls and the implant, and of movement of the fiber end relative to the implant surface for complete disinfection coverage thereof. The blade itself diffuses the UV light therethrough to increase contact surface area. Surgical instruments such as retractors may be used to separate the implant surface from the pocket walls for fiber insertion, but without removal of the implant.

For deeply implanted devices such as rods and hip and knee replacements endoscopic fiber carriers may be used, as described in the parent patent, for access to pathogenic (or possibly pathogenic) detected or suspected areas on such implants for disinfection. Because of the normally minimal depth of penetration of UV light, it can safely be used on accessible surfaces of implants for disinfection with minimal effect on surrounding tissues or cells.

Instrument Disinfection:

Disinfection of instruments with hard to reach or disinfect areas such as the biopsy or instrument channels of endoscopes was described in the parent application with the introduction of UV transmitting fiber through the channel at a rate sufficient to effect a substantially full sanitization. In embodiments herein such disinfection procedure can be enhanced (such as with shorter sanitization times or with the use of lower power) by physically pre-treating the inner walls of the channel such as with a thin absorbent string akin to a dental sponge-like "super" floss, a type of floss used to dislodge and/or remove any debris under and or around a dental "bridge" tooth with a circular brushing stroke or single, one-way, pull-through to blot up and/or disrupt any biofilm which may protect pathogens from the impinging UV light. Alternatively, existing disinfection procedures such as brushes which remove physical residue within biopsy channels but which are ineffective relative to pathogens may be utilized to enhance UV light pathogen disruption effect by disrupting light blocking biopsy films. It is understood that biopsy films develop and thicken over time and are normally not a significant concern with endoscopes which are disinfected immediately after each use before biofilm has formed to any detrimental extent. Occasionally, ineffective reprocessing procedures, however, leave pathogens in place, which does allow them to grow and build biofilms. Alternatively, a small rubberized collar around insertion strings or rods may similarly provide a "squeegee" biopsy film removal effect similar to window wiping. As a good prophylactic procedure, the endoscope channels should be internally exposed to sanitizing UV light prior to any endoscopic procedure.

Full Endoscope Disinfection:

Since endoscopes are primarily constructed of polymeric materials susceptible to degradation when exposed to UV light, the exterior of endoscopes have not normally been disinfected with UV light. In fact, studies have shown the detrimental effect of UV light on endoscopes. Though the channels of the endoscopes are lined with UV resistant PTFE, for purposes of reducing friction of inserted materials such as biopsy instruments, the exterior of an endoscope is fully exposed. Accordingly, the parent application describes the use of transmission media such as fiber optics to be inserted into such channels to direct UV light directly against the PTFE lining walls for disinfection purposes, without detrimental effect.

The studies showing detrimental effect of UV light on endoscopes, however, have specifically involved long term storage and exposure of the polymeric endoscope materials over extended periods of time of days. In accordance with another embodiment of the invention, the outer surfaces of endoscopes are exposed to UV light, and particularly UV-C light, for very short durations of at most several minutes and, depending upon exposure distance and power output, for even as little as seconds per exposure site. This is well short of the time necessary for UV light degradation of polymers by breaking of the polymeric bonds, in contrast to the very short time for DNA/RNA disruption resulting from phosphorus linkage breakages, as used for pathogen disinfection. In an embodiment, a ring structure of diameter sufficient to accommodate the cross-section width of an endoscope, a 360° internally directed UV light is used to disinfect an endoscope lowered therethrough (or the ring moved along the length of the endoscope) at a controlled rate. Because of the disparity in dimensions between endoscope insertion tube, body and handle, several light emitting rings may be utilized for the separate, differently sized components of the endoscope to maximize UV sanitization effect by close proximity. Alternatively, a flexibly expanding and contracting ring, with maintained full 360° UV light exposure, may be utilized to provide the full endoscope body with UV exposure for disinfection.

Increased Efficiency of UV Light Application:

In further enhancements of the disinfection processing of endoscopes and the like, a timed retraction mechanism may be utilized at the proximal end of an insertion fiber to move the fiber through an endoscope channel at a controlled rate sufficient to ensure more uniform and extensive UV light exposure to the interior walls of the endoscope channel for more effective pathogen eradication with significantly reduced opportunity for human error.

As a fail-safe method for ensuring disinfection, since disinfection provides no visible indications (procedures such as final ATP testing are helpful for certification of proper disinfection though such test are costly), UV light output is initially measured by a power integrating device such as an integrating sphere, an integrating non-spherical shape, or a calibrated UV intensity sensor, with the power output being calculated together with parameters of relative channel and fiber diameters to determine UV light distance application. If the pathogen is known, its susceptibility to being broken down by UV light can further be factored in, in a determination of the fiber dwell time and rate of retraction. In any event, large safety margins of time should be factored in to ensure that all pathogens likely to be encountered are eradicated.

A further embodiment of sanitization entails large scale simultaneous direct disinfection of device requiring cleaning such as cylindrical pipettes, catheters, syringes or similar laboratory or medical equipment with multiple UV fiber insertions and UV disinfection on an assembly line. Arrays of the devices are processed on a continuing basis on a conveyor belt with openings of the device facing in a parallel single direction whereby a corresponding array of UV light conducting fibers are lowered simultaneously into the array of devices, for a duration sufficient to disinfect each of the devices, and then lifted to permit the conveyor belt line to move a fresh array of devices into position for disinfection.

The above objects, features and advantages will become more evident from the following discussion as well as the drawings in which:

SHORT DESCRIPTION OF THE DRAWINGS

FIG. 1 schematically depicts a side view of a pulsed 266 nm laser, as immovably anchored with fixed optical connection to a fiber optic cable with pathogen disruption output;

FIG. 1A schematically shows the 266 nm laser of FIG. 1 with components of a 808 nm laser diode converted to a 266 nm laser output with output power measurement;

Figures 1, 1A:
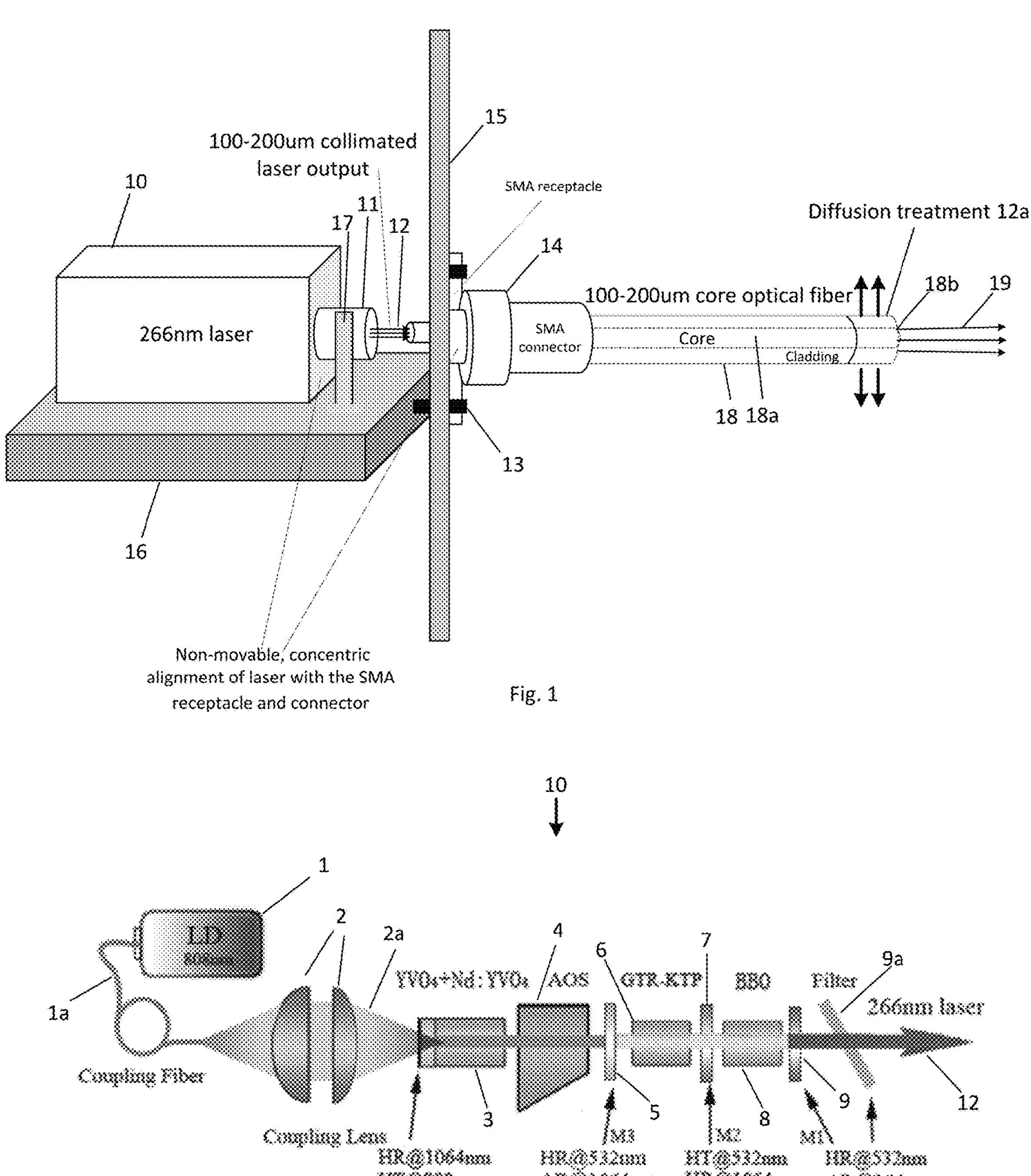
FIG. 1B illustrates a side emitting optical fiber modified to provide a uniform power output along its entire length.
FIG. 1C illustrates a stencil with fiber engraving lights for making the apertured side-emitting fiber of FIG. 1B.
Figures 2A, 2C:
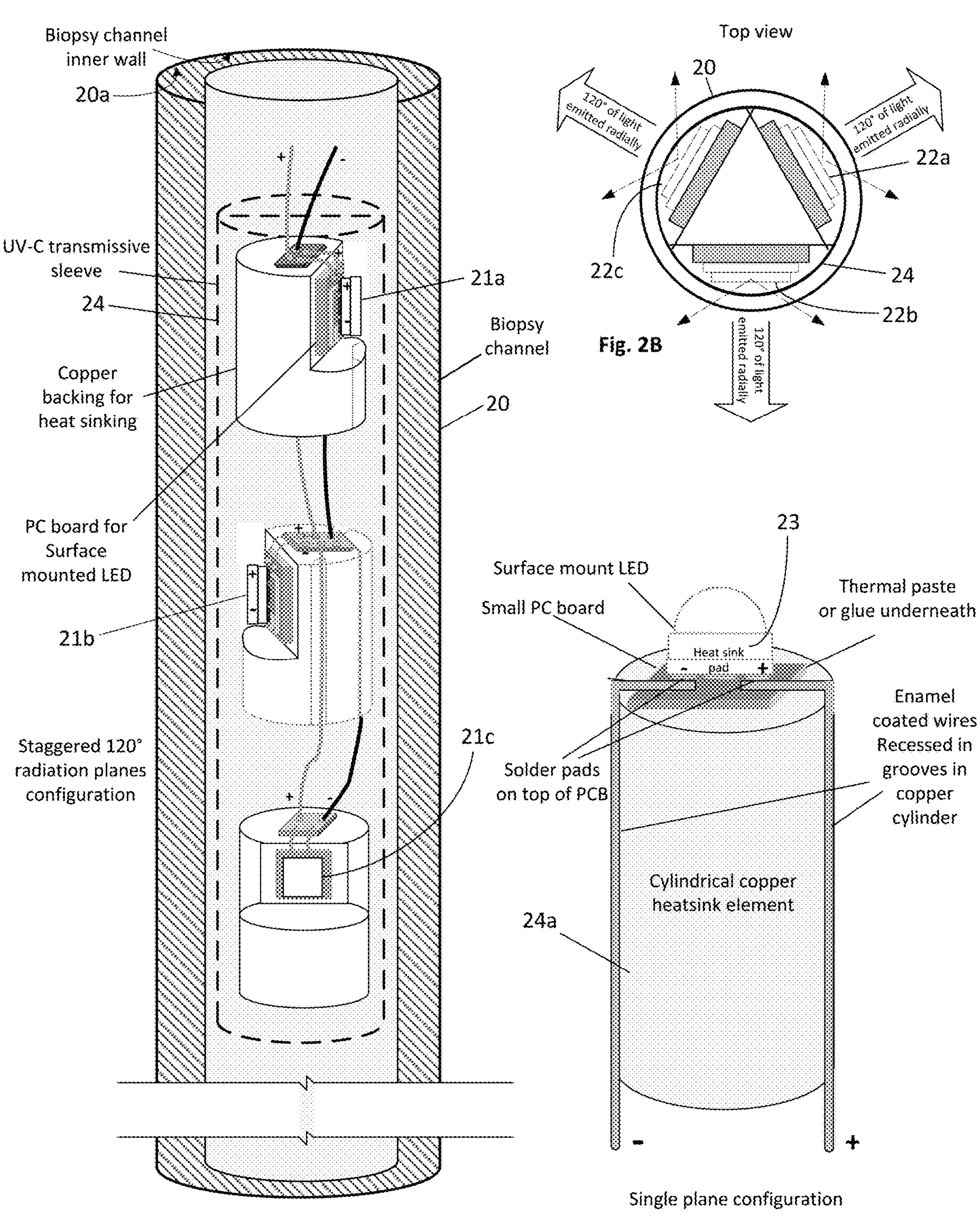
Figures 3, 3A:
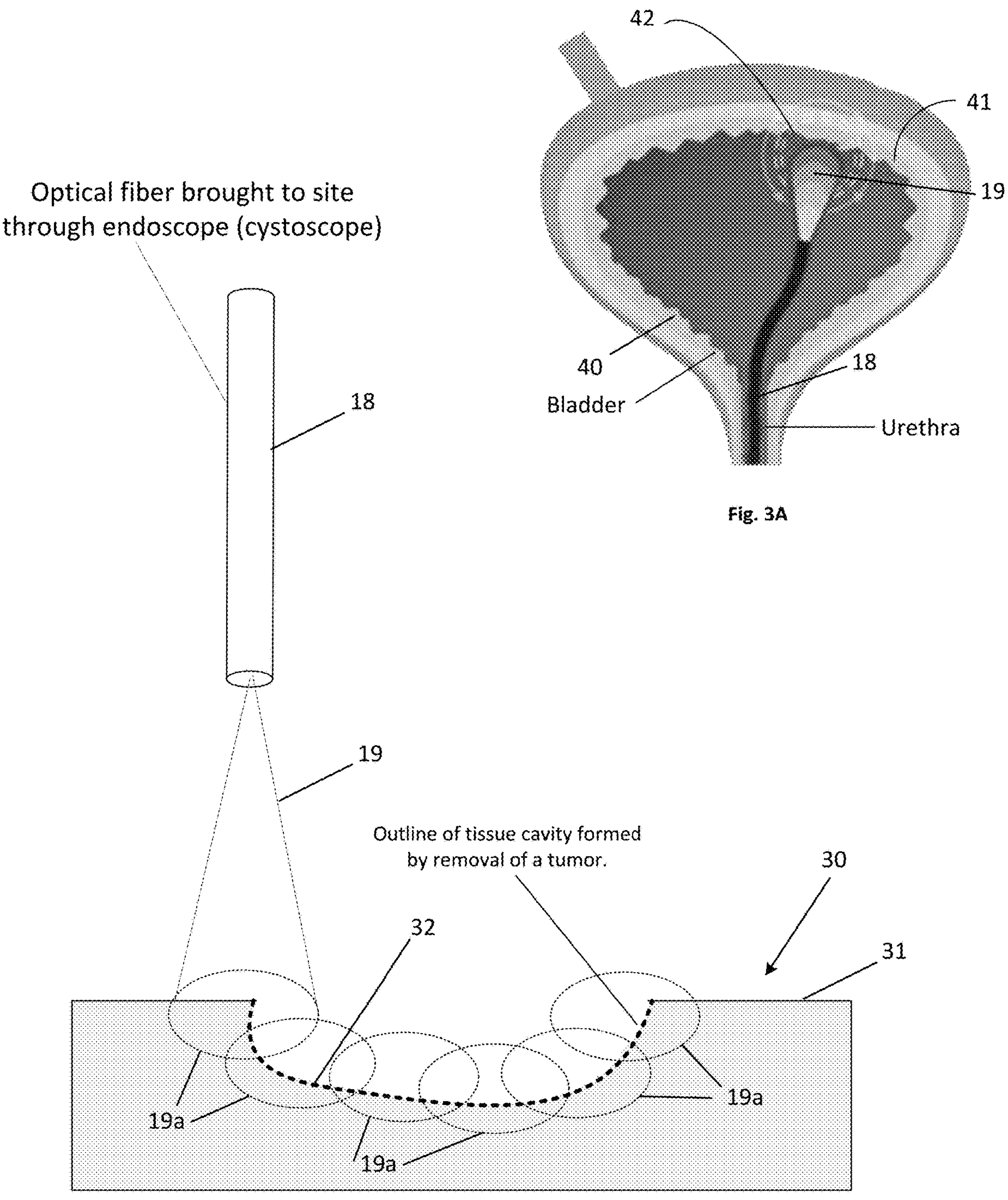
Figure 4A:
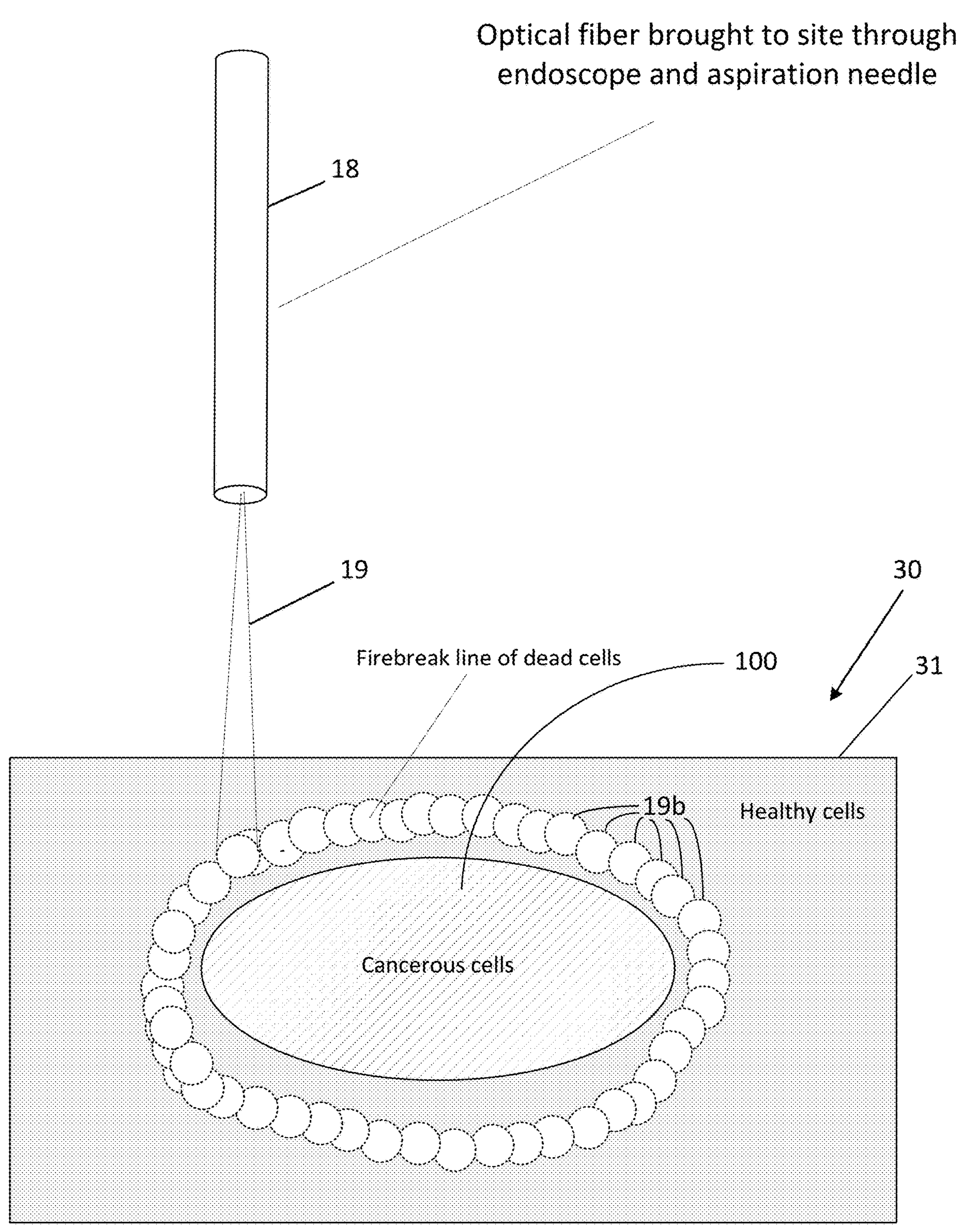
Figure 4B:
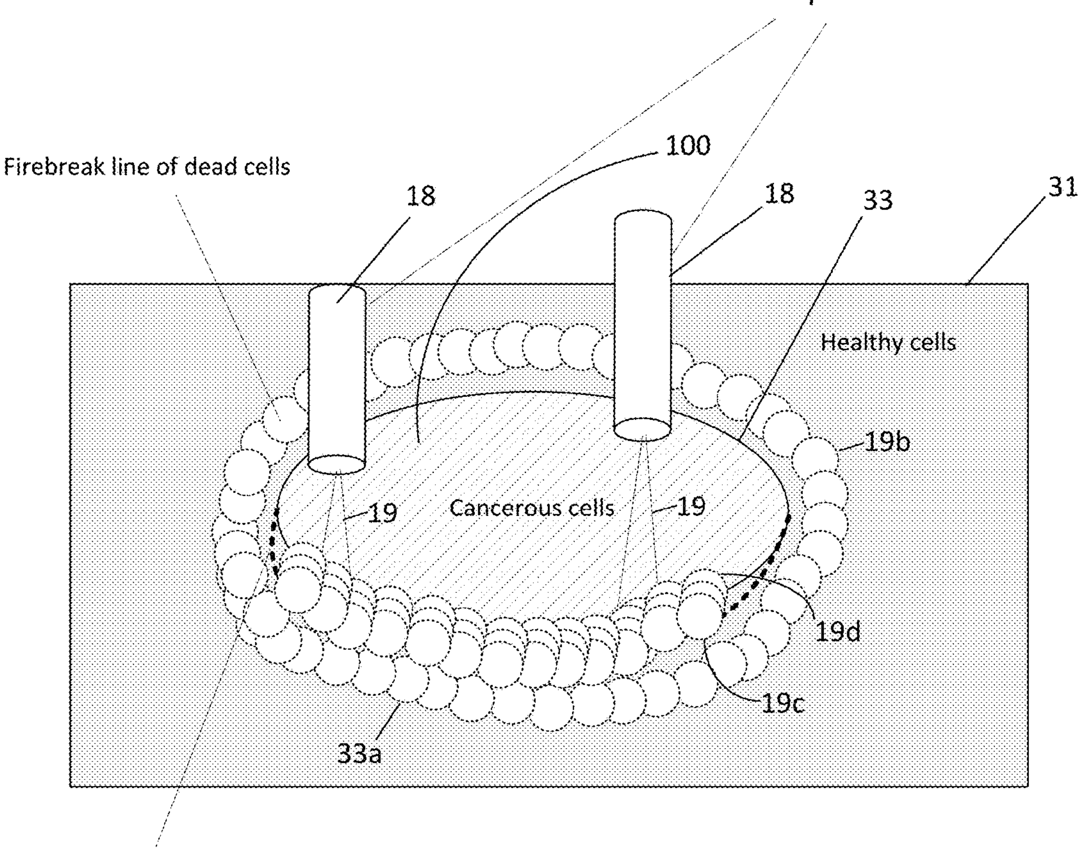
Figure 4C:
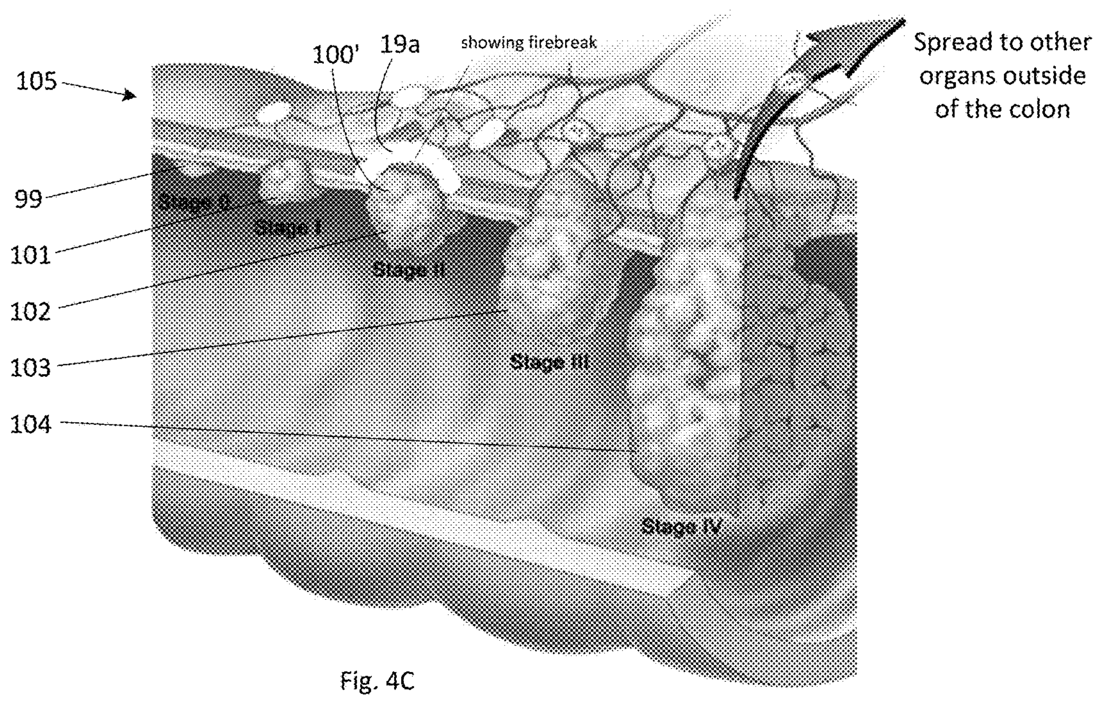
Figure 5:
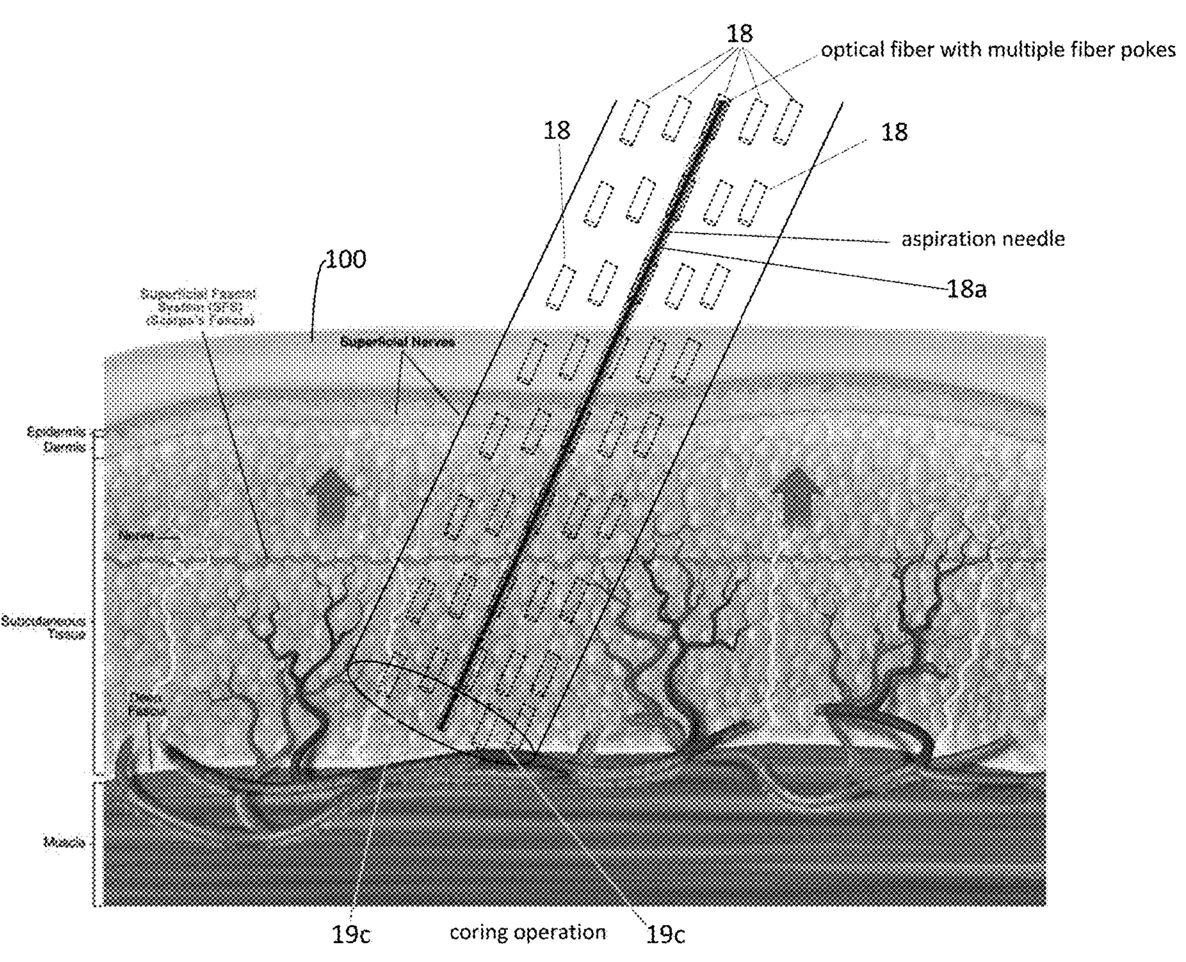
Figure 6A:
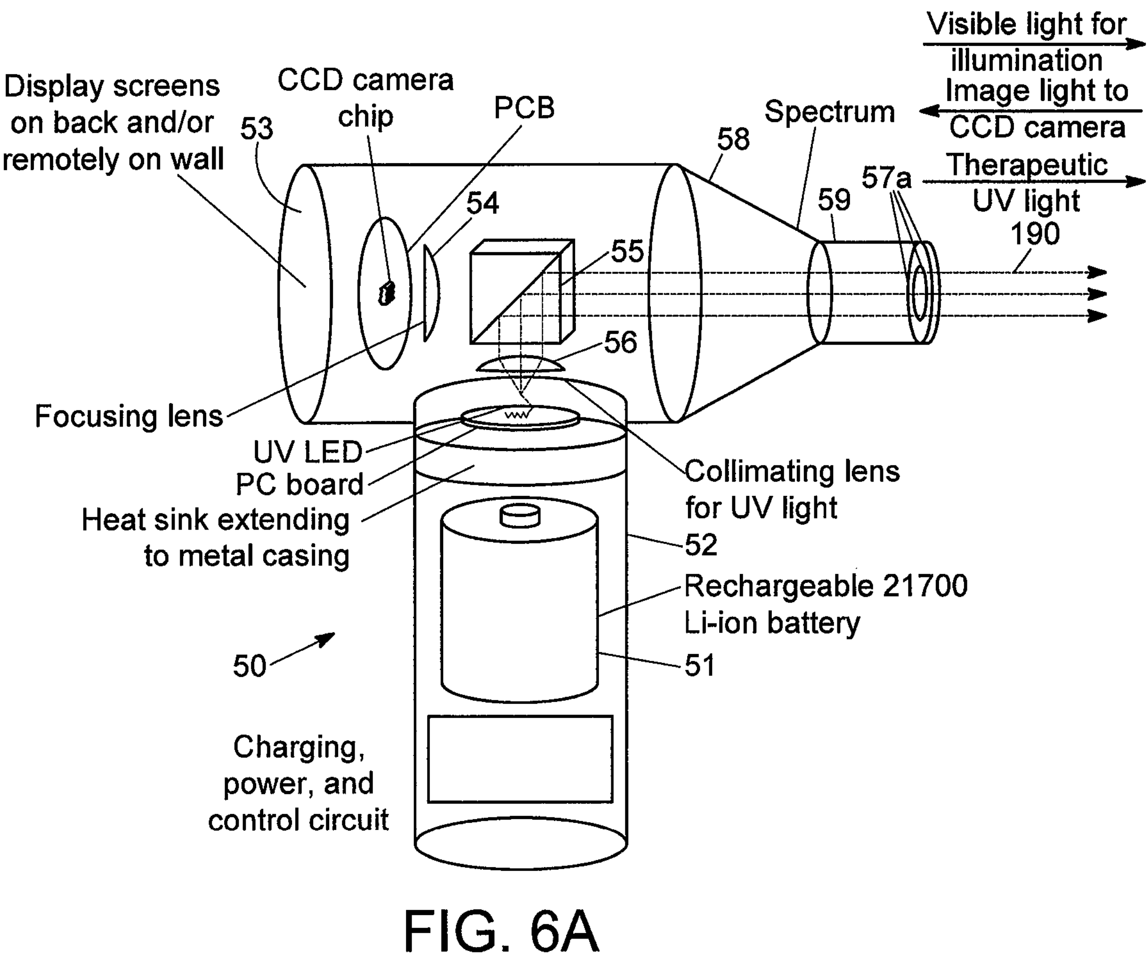
Figure 6B:
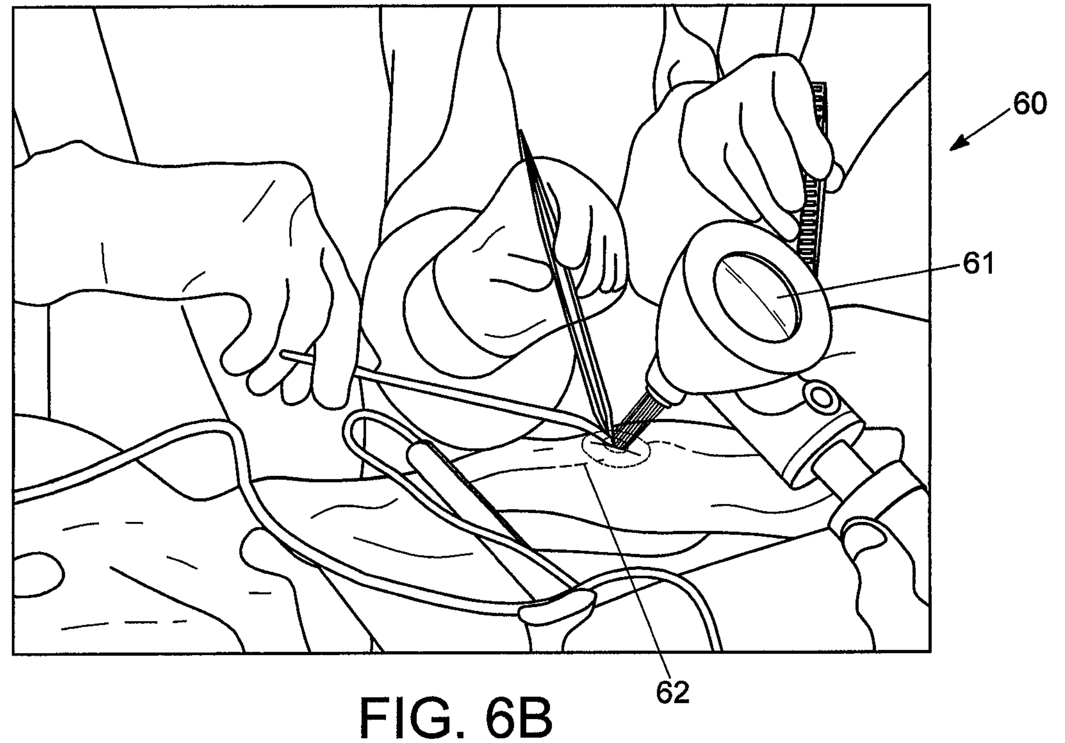
Figure 6D:
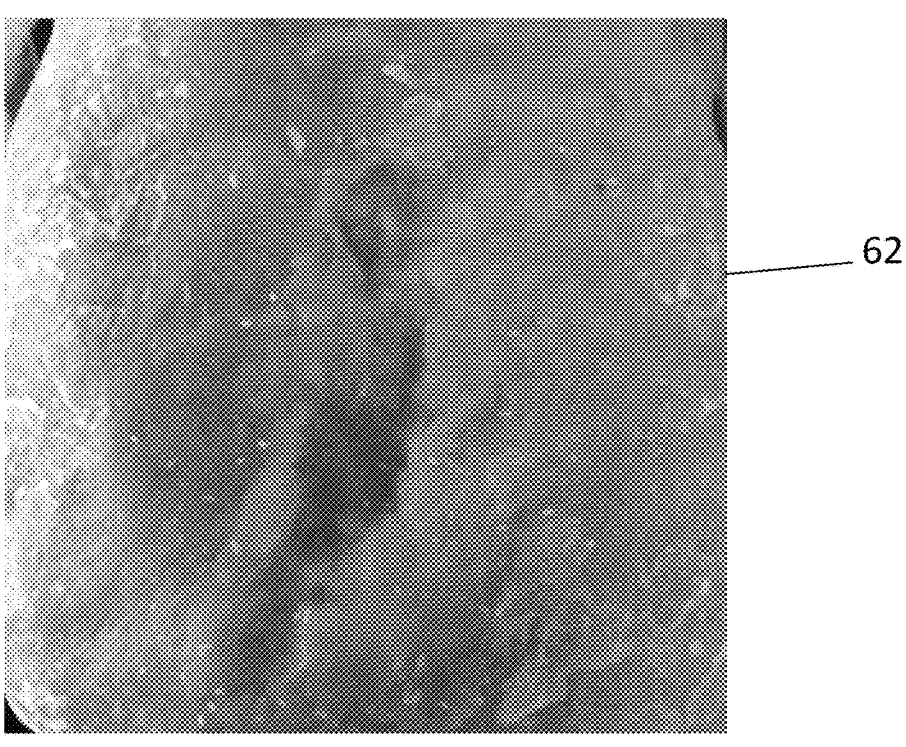
Figure 6C:
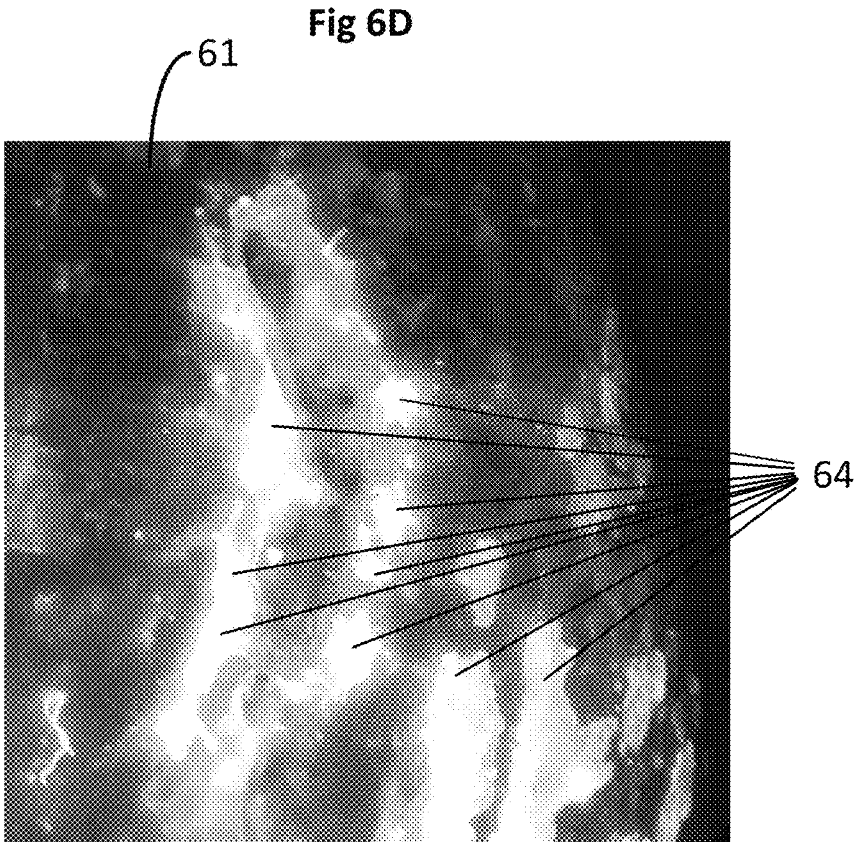
Figure 6E:
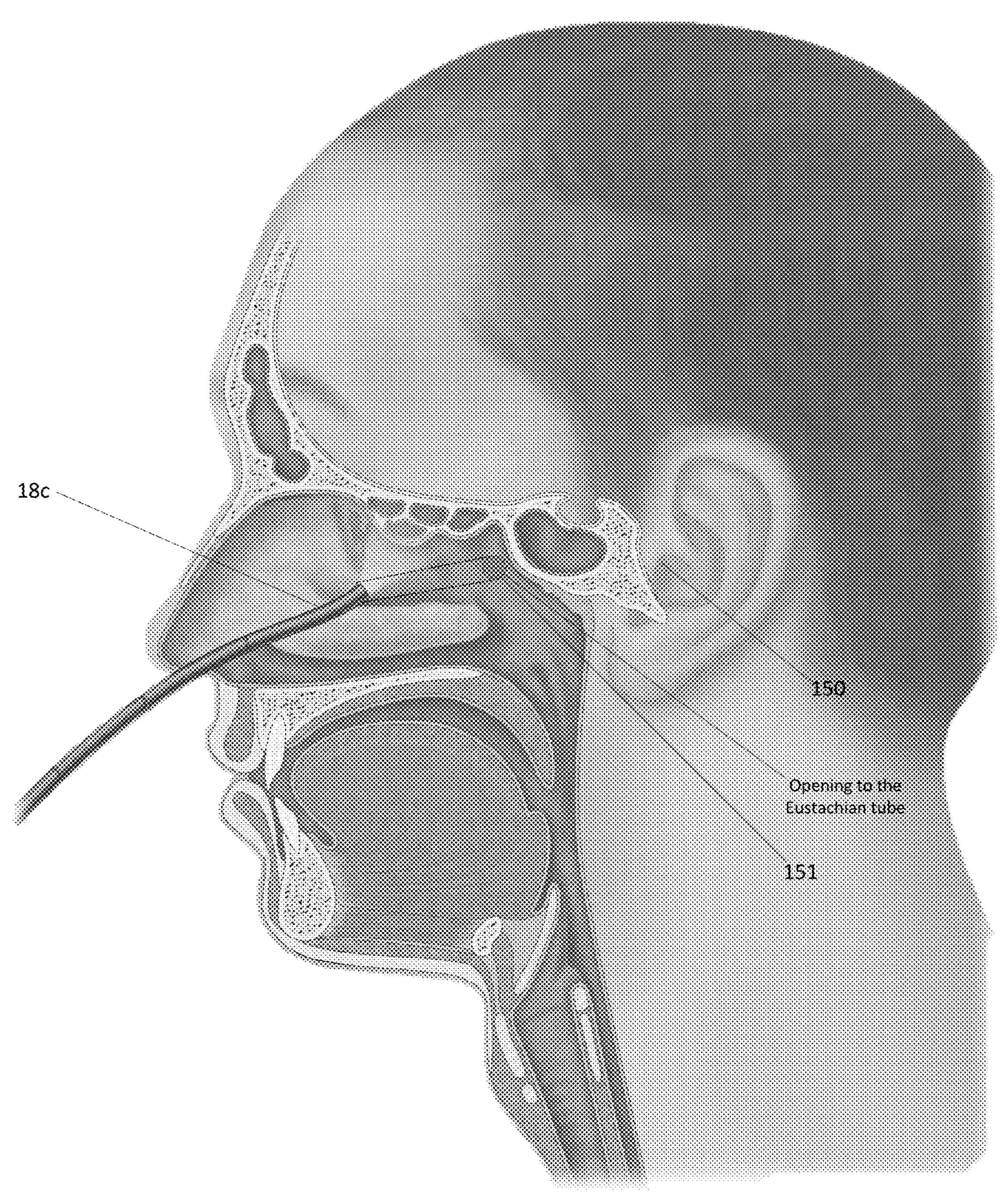
Figure 8A:
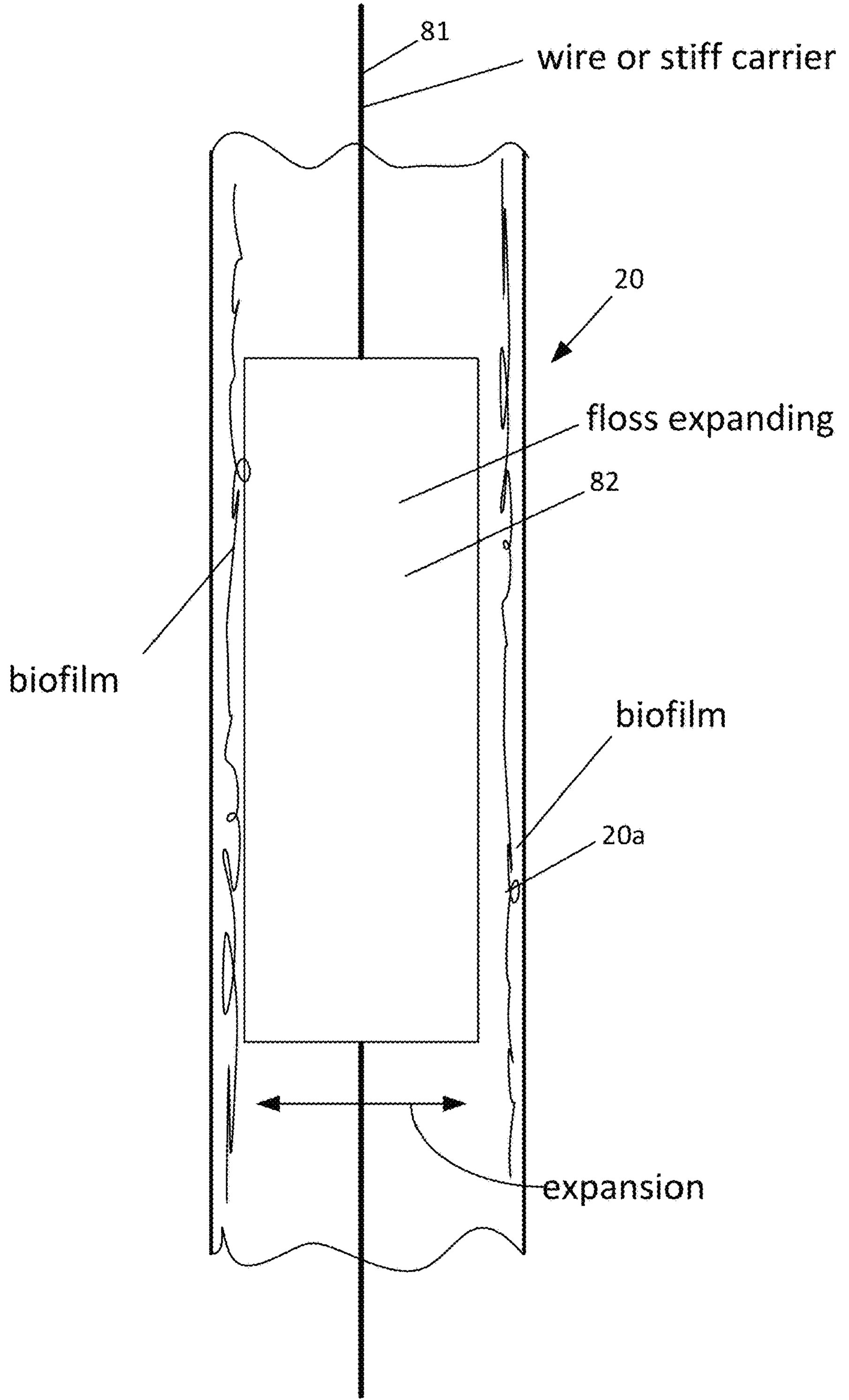
Figure 9B:
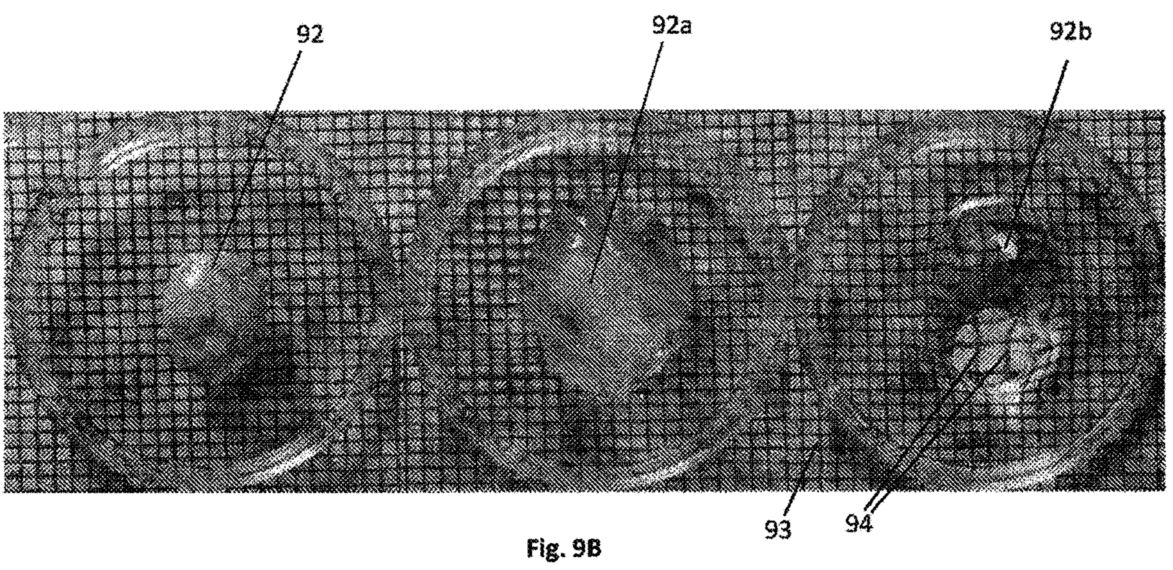
Figure 9C:
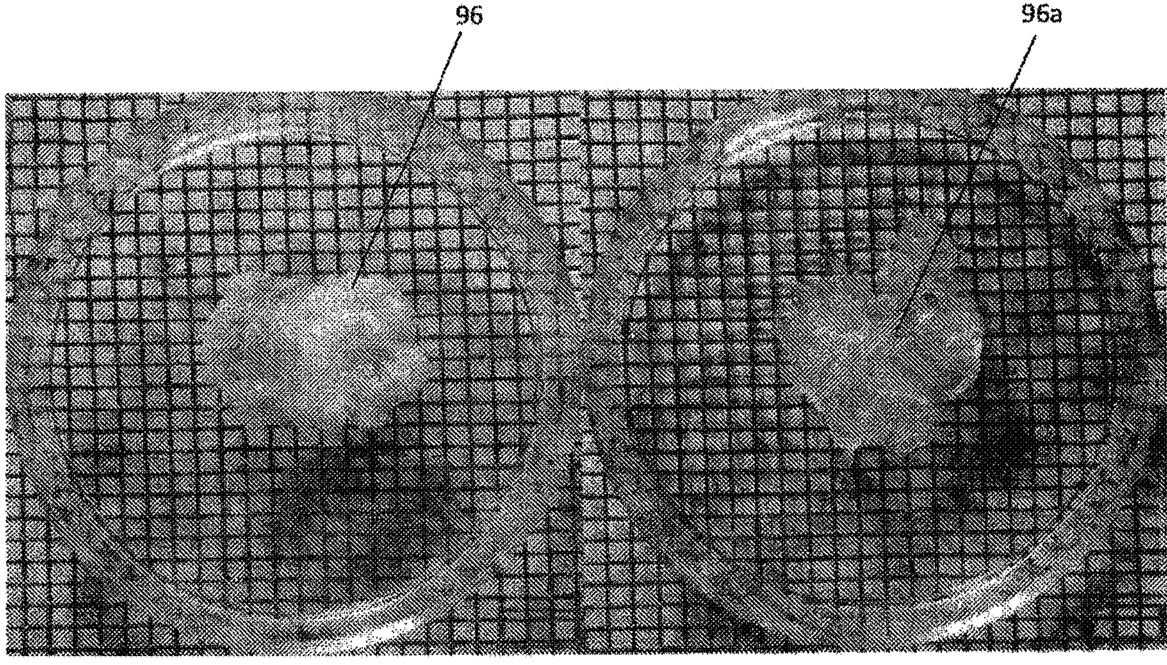
Figure 10:
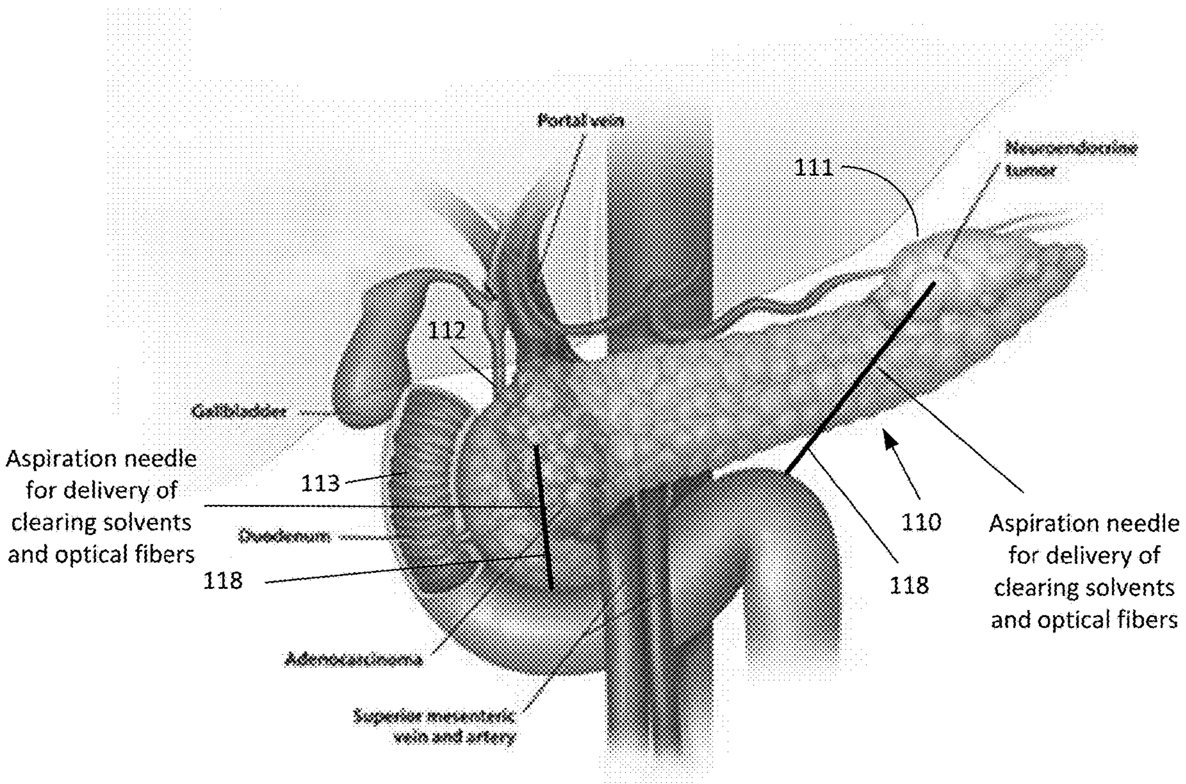
Figure 10A:
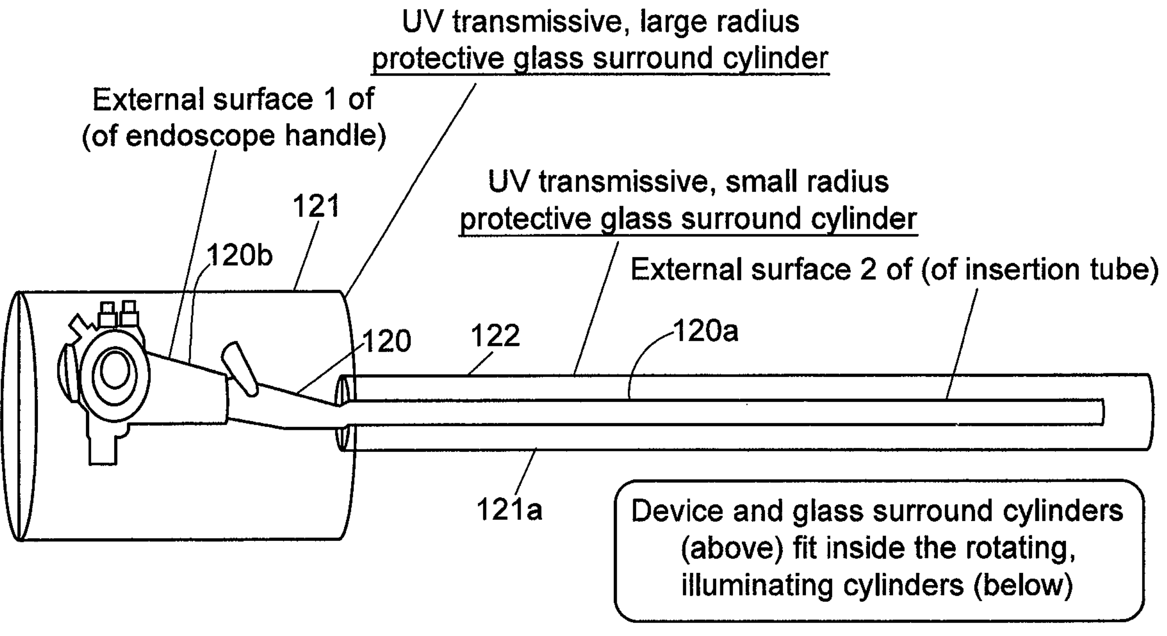
Figure 11A:
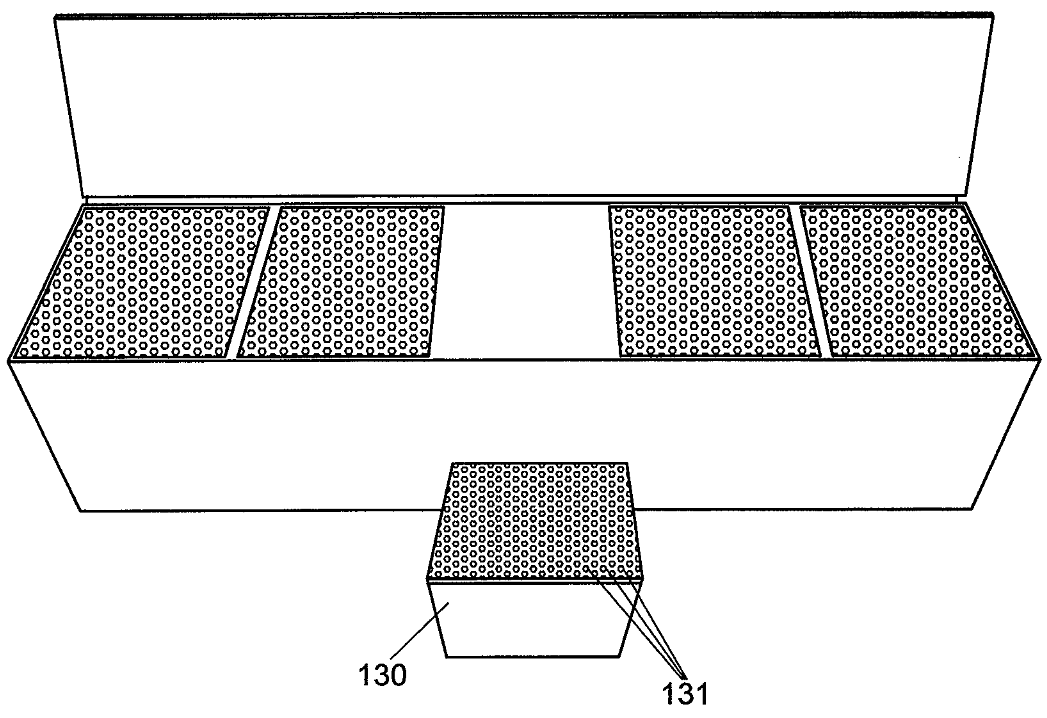
Figure 11B:
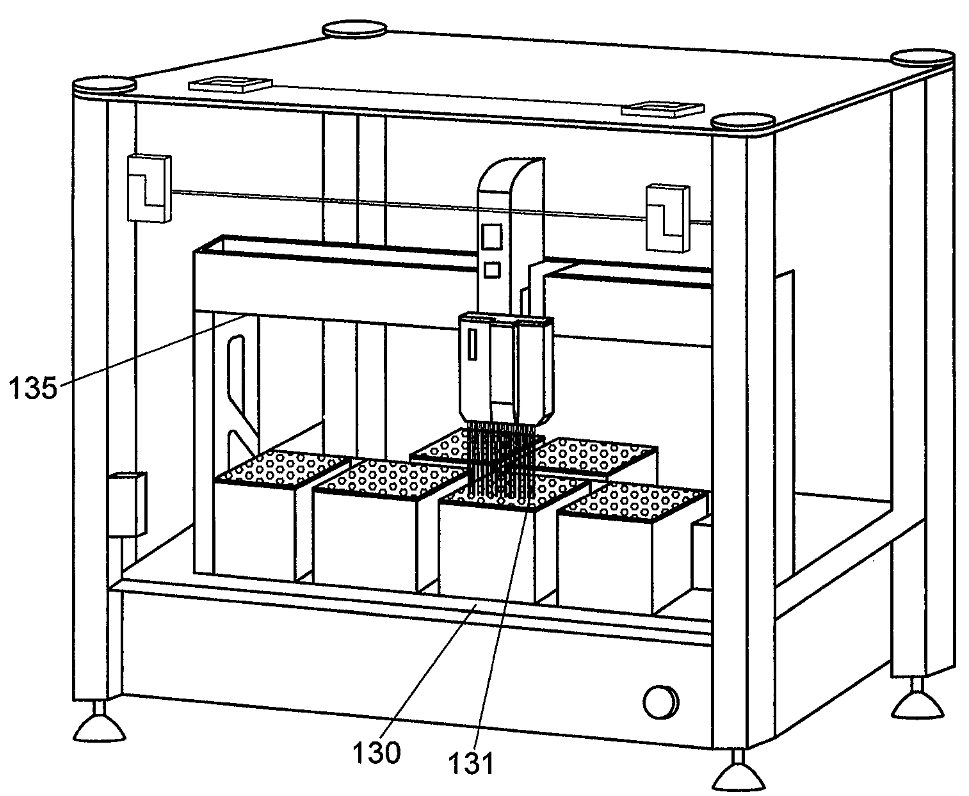
Figure 12A:
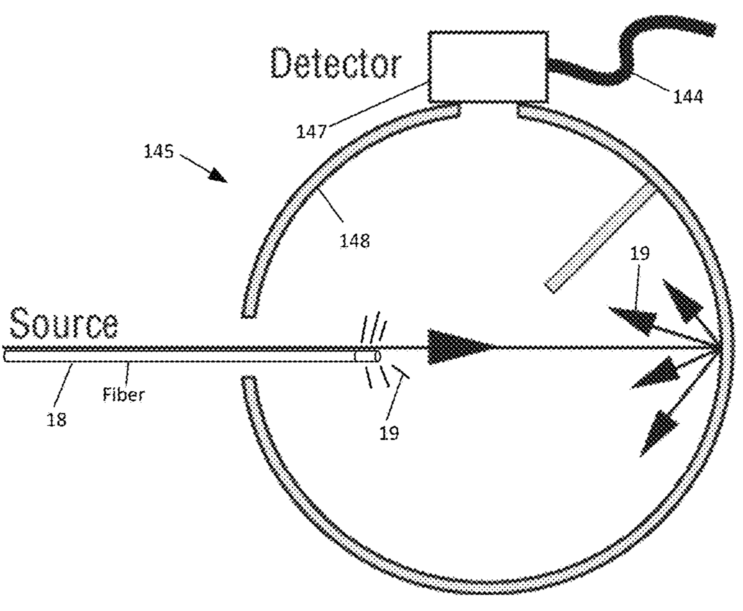
Figure 12B:
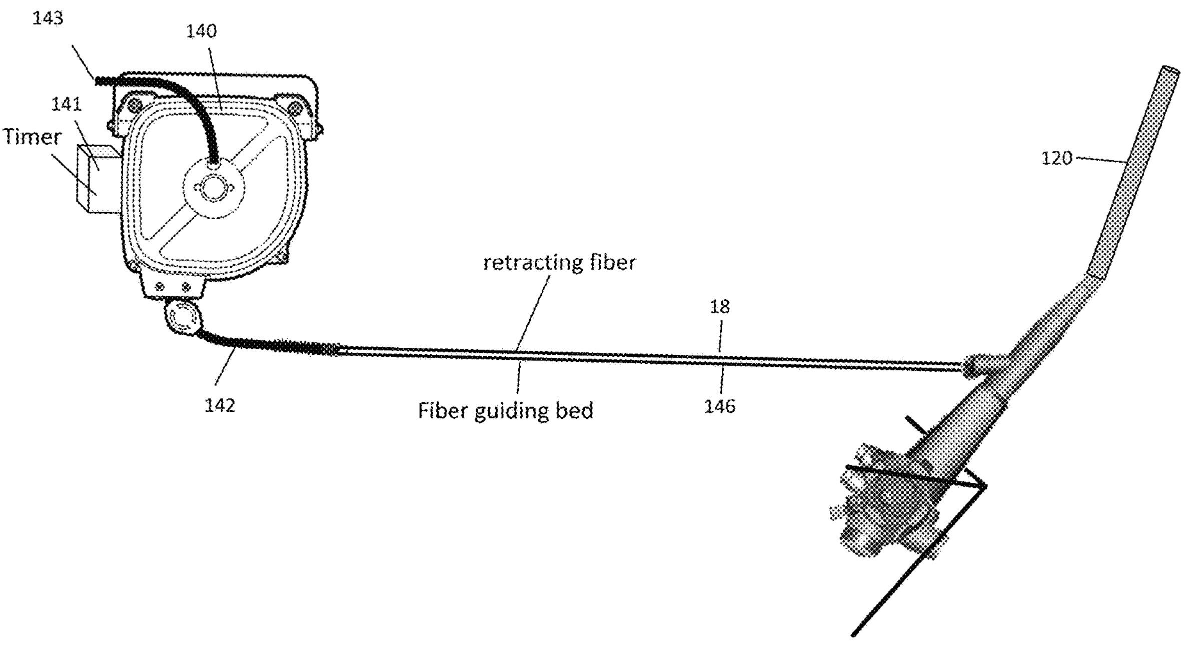
Figure 13A:
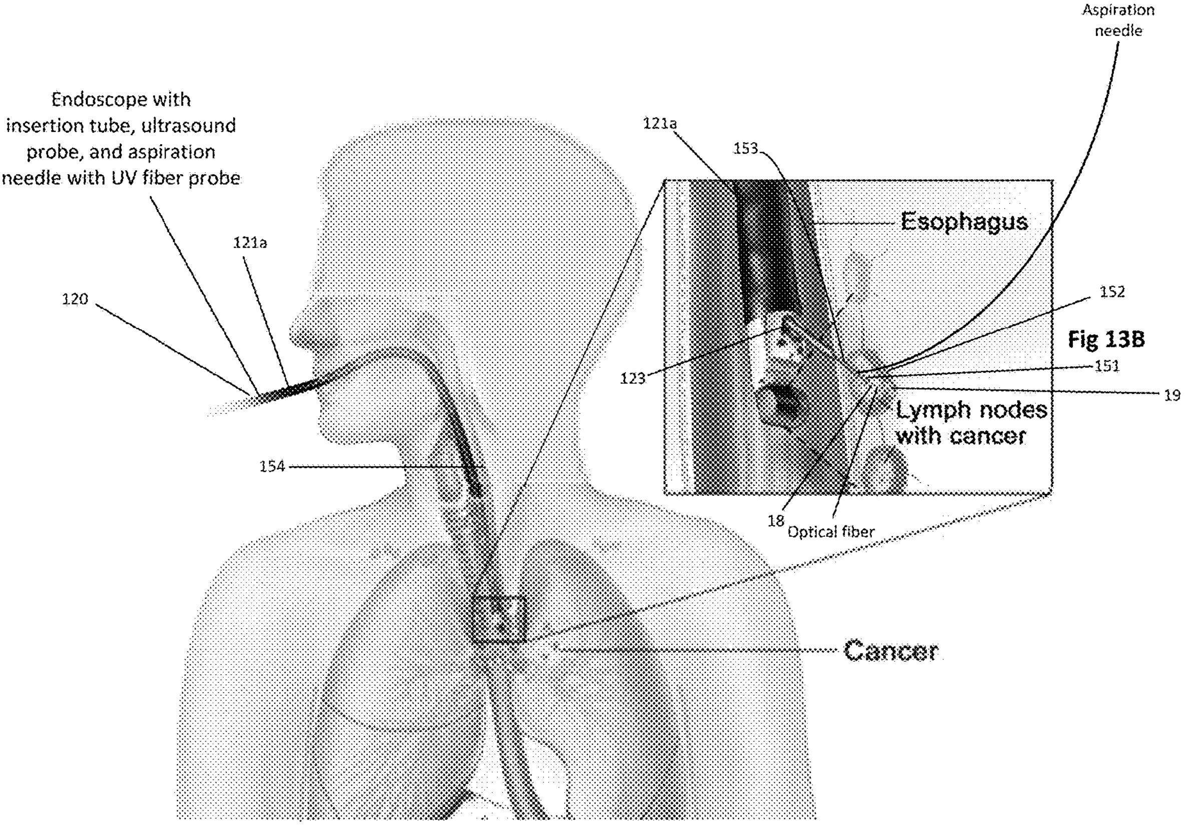
Figure 13C:
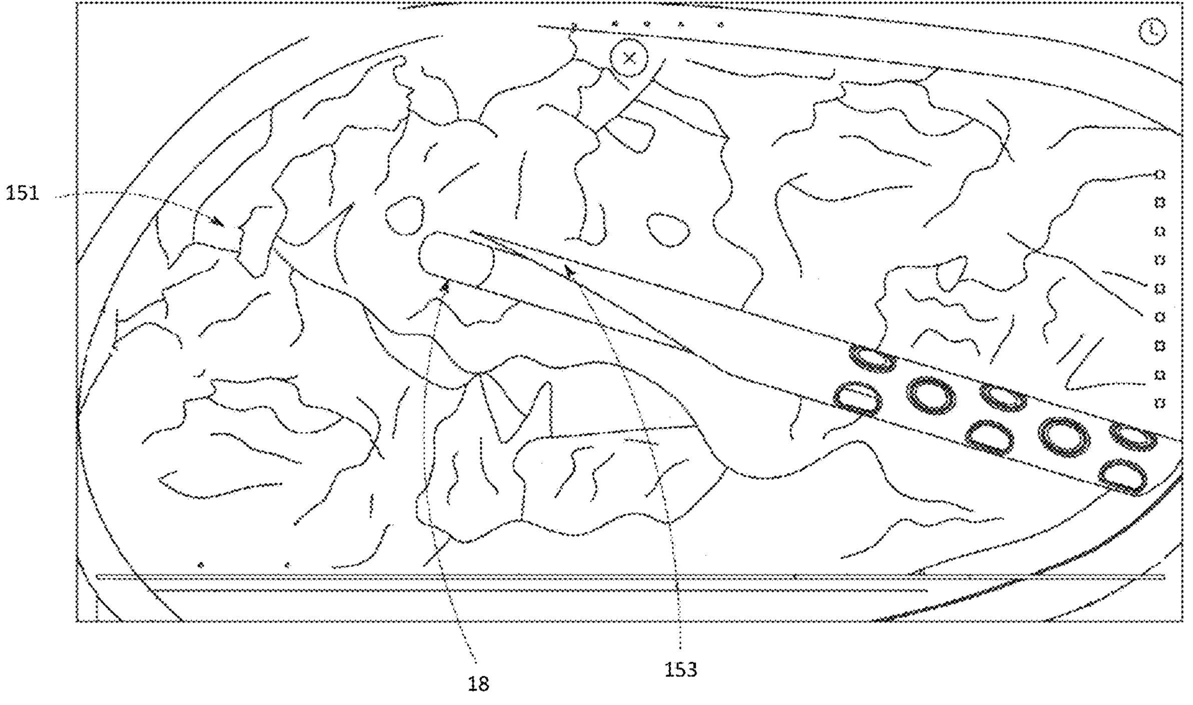

FIGS. 2A, 2B and 2C schematically depict a cross section of an endoscope biopsy channel with a three UV LED structure in a staggered plane (FIG. 2A side view) and in a single plane (FIG. 2B end view) with a 360° radial UV light output; with FIG. 2C (side view outside of a channel) depicting a single LED with forward spread UV light output;

FIG. 3 schematically depicts a side cross section view of an optical fiber directing UV light at a surgical site from which a tumor has been removed and FIG. 3A depict the application of a bladder with UV light being directed onto a site from which a cancer tumor was removed, for purposes of increasing length of remission;

FIG. 4A schematically depicts a view of an optical fiber directing UV light around the periphery of a tumor into healthy cells to provide an isolation of the tumor from the healthy cells, with FIG. 4B schematically depicting multiple depth peripheries of the application of the UV light around the tumor;

FIG. 4C shows an illustration of the tumor isolation of FIGS. 4A and 4B with a cross section side view of a colon showing varying stages of cancer development and an aspiration needle carrying a UV emitting fiber being used to form a dead cell and nutrient supply barrier between existing cancer cells and healthy cells with repeated insertions around the stage 2 tumor;

FIG. 5 depicts a multiple aspiration needle insertion of a cancer tissue coring operation which forms a widening lumen with repeated UV applications to kill surrounding cancer cells;

FIGS. 5A-C are cross section side views which sequentially schematically show the use of UV light in a raster procedure of removing cancer layers by disruption of RNA/DNA of cancer cells (FIG. 5A), then use of the UV light at high power to ablate and remove the dead cancer cells (FIG. 5B), and then using lower power UV light to again disrupt RNA/DNA of exposed cancer cells (FIG. 5C);

FIG. 6A shows a cross section view of an otoscope type instrument with UV light source and collimating transmitting lens being used to treat a sore throat;

FIG. 6B is a perspective view of a surgical operating site with the otoscope type instrument periodically bathing the surgical site with non-interfering disinfecting UV light from outside of the surgical instrument operation area and with a 405 nm LED light source for fluorescing bacteria;

FIGS. 6C and 6D are views of the display screen of the otoscope device of FIGS. 6A and 6B wherein the device emits light at a wavelength which fluoresces bacteria and the view originally depicting the non-fluoresced site (FIG. 6D) and depicts fluoresced bacteria at the viewing site for targeting (FIG. 6C);

FIG. 6E depicts a nasendoscope currently used for nasal, throat and larynx treatment with inner ear reach, retrofitted with UV light emission for disinfection and bacteria infection treatment of such sites, and as being used for nasal disinfection;

FIG. 7 depicts a UV light carrying fiber being directed by a laparoscopic procedure to be positioned adjacent an infected medical implant pacemaker for the disinfection thereof by LV light in situ;

FIG. 7A is side section view of the medical implant pacemaker in a pocket between skin and muscle with insertion of the UV transmitting light fiber between the pacemaker and skin and pacemaker and muscle in the holding pocket;

FIG. 8 depicts a pre-UV light treatment elongated element with expansion element for disrupting bio-film in an endoscope biopsy channel and FIG. 8A shows it in position in expanded form for effecting the bio-film disruption;

FIG. 9 is a flow chart showing steps for removal of lipids and pigments from cancer tissue rendering it more transparent with less scattering of light from contained lipids and less light absorption by pigments allowing greater UV light penetration;

FIGS. 9B and 9C respectively show prior art tissue clearing progression over time of a mouse brain (FIG. 9B) and a tumor (FIG. 9C), to transparency;

FIG. 10 shows a cancerous pancreas with duodenum access for an aspiration needle for de-lipidation and removal of pigments and subsequent insertion application of UV light;

FIGS. 10A-D show a full exterior of an endoscope being disinfected with timed endoscope insertion through a ring of UV light with minimized distance of UV surface applications, with FIG. 10A showing an endoscope contained in a protective glass and then rotated in a correspondingly sized cylinder with internal LEDs (FIG. 10B), and a vertically hanging endoscope with a small ring of LED lights being moved along the outer surface of the insertion tube (FIG. 10C) and a larger ring for the handle (FIG. 10D);

FIG. 11A shows a batch tray with an array of pipettes requiring disinfection and FIG. 11B depicts an array of pipettes being simultaneously disinfected with fiber insertion and UV treatment in batch trays on an assembly line with pipettes positioned for simultaneous disinfection with a movable matched array of UV transmitting optical fibers;

FIGS. 12A-B show a biopsy channel disinfection procedure with the device of the invention starting with power output determination (FIG. 12A), as an alternative to the integrated power measurement of FIG. 1A with FIG. 12A showing the free end of the fiber coupled to a UV light source inserted into an integrating sphere with power reading, with FIG. 12B showing the fiber inserted fully into an endoscope biopsy channel and being extracted by a retractor, with timing mechanism, on a linear track and moving at a calculated pre-determined rate;

FIG. 13A depicts the insertion of an aspiration needle through an endoscope into lungs for treatment by UV light of cancer in lymph nodes, with FIG. 3B showing an expanded view of section A in FIG. 13A; and FIG. 13C shows an expanded view of a UV fiber as carried by the aspiration needle of FIGS. 13A and 13B.

DETAILED DESCRIPTION

With reference to the drawings, FIG. 1 depicts a UV light emitting laser 10 with a 266 nm wave-length light (at or near the optimal DNA/RNA disruption level of 265 nm). The emitted UV light 12 is collimated and is in the form of a narrow beam of 100 to 200 microns which is optically aligned at brace 13 with an optical fiber 18 of the same or greater diameter through an appropriate acceptance angle (defined as an input angle which permits light to be accepted for output at the distal end of the fiber). With such small dimensions, the laser beam cannot be susceptible to slight movement which could cause the beam to be improperly angled and absorbed by the protective fiber optic shielding. Accordingly, the fiber 18 is locked into essentially non-movable position such as with glue or connectors to rigidly fixed brace 15, without play such as with the SMA connector 14 shown. The laser 10 is similarly locked into position on support 16 and with bracing element 17 locking output 11 in position. Though laser light 12 is collimated and non-diffused, its passage through the fiber 18 diffuses it slightly at the output 18*b* by about 0.5° in each direction. Further diffusion, as required for effective disinfection, is obtained by treating the distal or emitting end of the fiber 12*a* to effect light diffusion of desired spread. Alternatively, as shown in FIG. 1B, light may be emitted along substantially the entire length of the fiber.

FIG. 1A shows the components of laser 10, starting with laser diode 1 with 808 nm (which may also range up to 885 nm) with light output channeled via coupling fiber 1*a* into coupling lens 2 with the output light being focused at 2*a* into crystals 3 and 4 and conversion to 1064 nm and filter 5 into crystal 6 for second conversion to 532 nm. Thereafter, the light passes through crystal 6 and filter 7 and BBO crystal 8 and filter 9 to 266 nm laser output. Beam splitter 9*a* pulls some light out for measurement of power and the remaining light exits as laser light 12 at a 266 nm UV laser light output.

Figure 1B:
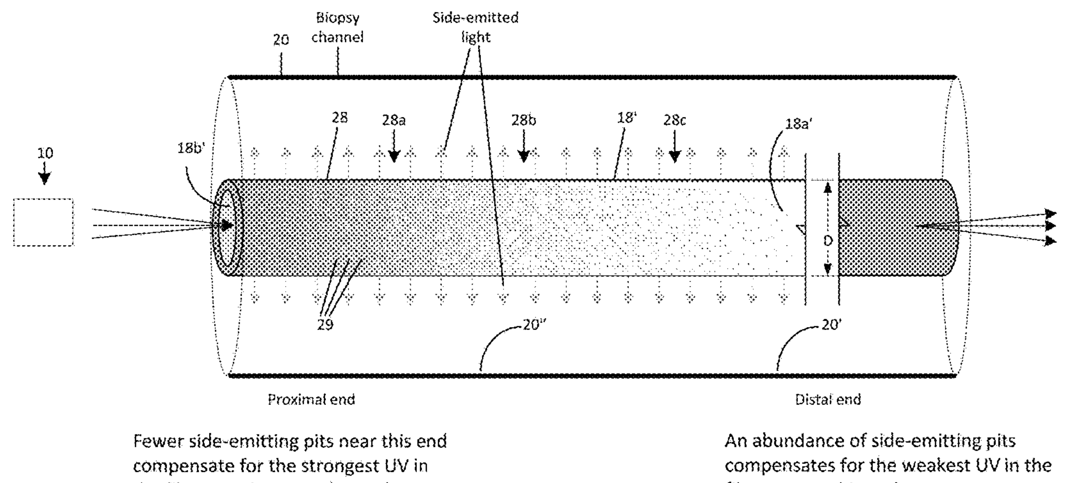

FIG. 1B shows a side-emitting fiber 18' with cladding 28 which is perforated with microdot holes 29 to expose the fiber within the cladding for substantially full side emission of UV through the microdot holes with substantially uniform power output, as shown (or otherwise predictably controlled) output intensity. Though the microdot holes create small openings so that some of the light and output intensity can be emitted, the fiber remains sufficiently structurally sound to provide protection to the fragile fiber core. Effective pathogen eradication can be provided with such fiber structure with the use of a high-powered light source such as a laser or a high powered LED.

Figure 1C:
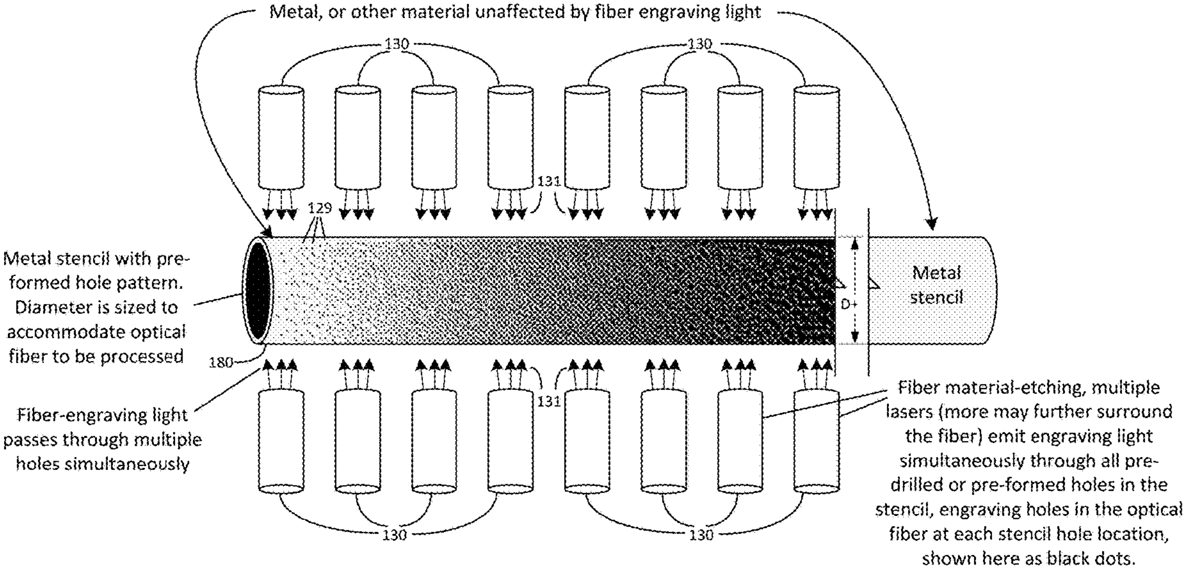

FIG. 1C shows cylindrical stencil 180, configured with calculated hole placement, and with an appearance corresponding to the fiber 18' shown in FIG. 1B (with stencil holes 129 corresponding to the microdot holes 29 formed in the fiber 18') is used to form the array of microdot holes 29 in a desired configuration on the fiber 18'. The cylinder 180 is of slightly larger diameter D+ than the diameter D of fiber 18' and sufficient for it to enclose the fiber 18' therewithin during etching microdot hole formation. Stencil cylinder 180 is of a laser-etching impermeable material such as of metal (the laser light etchers 130 are configured to etch or perforate glass of the fiber buffer and cladding). Glass etching laser light 131 is trained on the stencil enclosed fiber to efficiently form the microdot holes 29 through stencil holes 129 in a desired configuration such as shown in FIG. 1B. Multiple laser etchers 130 surround the stencil to efficiently form the requisite microdot holes in the fiber 18'.

Simple side emitting of light (as in the prior art with LEDs with output in the range of 65 mW) or with uniform density of microdots (not shown) results in a structure which emits light from the side with drastic reduction in output intensity, with greater distance from the light source, often petering out to little or no pathogen eradication light emission at a distal end of an 8" fiber. Density of graduated microdot holes distal end section 18*a*' of fiber 18' in section 28*c* emits at least milliwatts of UV light emanating originally from laser 10 whereby the distal end 18*a*' effectively disinfects the distal end 20' of biopsy channel 20 in minutes. The remaining sections 28*a* and 28*b* of fiber cladding 28 are configured along an appropriate calculated side emission power curve to be more opaque with fewer microdot holes to compensate for greater power emission of UV light from fiber section 18*b*' closer to the UV laser light source 10 and a substantially uniform side output power along the length of the fiber.

With an endoscope biopsy channel 20 or catheter of relatively large diameter, e.g., 4 mm or more, an offset linked vertical series of UV LEDs 21*a*, 21*b* and 21*c* contained within a transparent UV light transmissive sleeve 24 are inserted into an end of a biopsy channel 20 as shown in FIG. 2A. The LEDs each face the inner wall 20*a* of the biopsy channel and are offset from each other by 120° to ensure a 360° degree total UV light coverage of the inner wall 20*a*. During disinfection the LEDs are initially fully rotated to ensure full UV light coverage at the resting base of the LED stacked series prior to disinfection extraction.

In FIG. 2B an end view of the biopsy channel 20 shows an inserted alternative single planar version of the three LEDs 22*a*, 22*b* and 22*c* arranged in a single plane in a triangle configuration whereby the LEDs emit UV light respectively against the inner wall of the biopsy channel 20*a* in respective 120° angles.

FIG. 2C depicts a single LED 23 atop a cylindrical copper heat sink structure 24*a*, sized to be longitudinally placed in a biopsy channel with the LED providing a conical circular UV light output at an angle which impinges on the wall 20*a* of a biopsy channel into which it is inserted.

Though the LEDs, because of size constraints, are of lower power in sizes suitable to fit within the channel, full power without attenuation losses is directed against the channel walls. The LED arrangement is provided with power input and with a sufficiently rigid positioning rod, wire or cord, used for placement and controlled movement (not shown).

FIG. 3 schematically depicts a cancer tumor site 30 with a tumor having been surgically removed and the removal area 32 is shown in phantom in dashed lines. UV light 19 directed from a fiber 18, brought to the tumor removal site 30 by an endoscope (not shown), is prophylactically spread over at least the tumor removal and adjacent areas 32 and 31, as depicted by the circular areas 19*a* to retard return of aggressive cancers and increase duration of remission. This is akin to BCG treatment of bladder cancer sites with a surface treatment to prevent recurrence. The site treatment may be used in conjunction with or in place of current surface treatments.

FIG. 3A illustrates the schematic procedure in FIG. 3, wherein a bladder 40 has a removed tumor at site 42 on the inner wall surface 41 of the bladder. UV light 19 from fiber 18 inserted through urethra 43 is trained at least on the site 42 and surrounding tissue of wall surface 41 to maintain remission and prevent tumor regrowth.

A cancer treatment protocol is schematically depicted in FIG. 4A wherein a cancer site 100 perimeter or interface 33 with healthy cells is detected and defined by biopsy procedures. UV light 19 from fiber 18 is directed at healthy cells 19*b* adjacent the interface perimeter, to form a separating line of dead cells 33*a* or "firebreak", with disruption of cell nutrient pathways therein. As shown in FIG. 4B, with surface treatment being about 40 microns, greater depth for the "firebreak" or cancer expansion barrier is effected with an aspirating needle 18*a* extending contained UV light directing fiber 18 (carried to the site by an endoscope, not shown, through its biopsy channel as described in the parent application) which pierces into the area 31 at a lower depth of the interface to increase the depth of the "firebreak", as shown, with increasing depth at 19*c* and 19*d*. Spreading of the cancer cells is contained thereby with a limitation on metastization. Phagocytes, which remove the dead cells provides a separation between cancer cells and healthy cells and blood vessels with nutrient supply is also disrupted in containing cancer growth and spread.

FIG. 4C is a sectioned depiction of a colon 105 showing various stages of cancer tumor growth ranging from non-colon-surface-penetrating tumor 99 to stage 1 (101) with slight surface-penetration to stage 2 (102) with surface layer penetration and stage 3 (103) full surface layer penetration and stage 4 (104) with full penetration and extension outside of the colon with spreading to other organs (metastization). Stage 2 cancer is illustratively shown (since the colon has a lumen and the cancers are surface type cancers surgery is best for removal) for treatment by the treatment protocol of FIGS. 4A and 4B with multiple needle penetrations with UV deployment from fiber 18 (19*a*) of the tissue around tumor 102 in order to build the "firebreak" of a dead cell barrier around the tumor to retard further spread of the cancer to surrounding colon surface tissue.

FIG. 5 illustrates another UV treatment protocol of a cancer site 100 with full needle penetration of the tumor 100 itself by aspiration needle 18*a* and then extending fiber 18 to laterally treat surrounding tissue. As shown in dashed lines, needle 18*a* with fiber 18 is withdrawn and inserted numerous times around the initial needle deployment to provide a coring treatment with expanding core areas of dead cancer tissue 19*c*. Ablative removal of cored tissue is effected through secondary needle deployment in the core area with applied suction or fluid washing (or phagocytes allowed, in time, to remove the dead cells) to widen a small lumen within the tumor to allow for increasing widening of the UV treatment and successive disruption and formation of dead cell layers for continued removal. FIGS. 5A through 5C illustrate such widening cancer cell removal with fiber 18 shown as directing UV light on (or in) cancer tissue of cancer 100 which is located in healthy cells 31 (the cells are schematically depicted as building blocks of light and dark bricks of healthy cells 31 and cancer cells 101*a* respectively). Raster deployment of UV light 19 at a disruption power level kills the cancer cells in the layers exposed to the UV light (FIG. 5A) and the dead cells are then treated in a raster deployment by ablation power levels of UV light 190 with dead cells removal by a fluid wash and/or suction as shown in FIG. 5B. The power levels of UV light disruption (generally in the double digit milliwatt range) are sufficient to kill cancer cells which cannot self heal as compared to healthy cells which can. Dead cells have lessened intercellular adhesion and are more easily ablatively removed. The disruption/ablation raster procedure is repeated (preferably automatically or robotically to successively kill and ablatively remove cancer tissue cells 100*a* as shown in FIG. 5C to lessen tumor size or to remove it.

Non traumatic removal of cancer cells is shown in the sequential depiction of FIGS. 5A-C in which a surface layer of cancer cells is treated with UV light to the point of DNA/RNA disruption and eradication (FIG. 5A). Thereafter, UV power level is raised to minimal ablative power and trained on the dead surface cancer cells to effectively sweep them away (FIG. 5B). The exposed new surface of the cancer cells is then again treated with UV light with a raster-like repetition of disruption and ablation. Depending on duration of each of the cycles and assuming a ten second period of the cycles and a 40 micron removal for each cycle, removal of a 1 cm thick cancer layer requires about 2500 seconds or about 42 minutes of total treatment per cancer site. The disruption is on a molecular level and not physically discernable and the ablative cycles are at minimal effective power to remove dead cells (less power than required to ablate live cells) with minimal trauma, if any, and certainly much less than standard radiation therapy by orders of magnitude. The endoscope carrying the optical fiber used for the disruption/ablation procedure has water, air and suction channels which are used during or after ablation procedures to facilitate cleaning and removal of dead cells with exposure of additional cell surfaces. Bio-feedback such as cancer cell luminescence provides visible indications of the effect of the cancer cell removal.

FIG. 6 shows a cross section view of an otoscope type device 50 generally used for the application of light into externally exposed orifices such as respiratory, alimentary and excretory orifices and viewing of these sites. The device is modified for the effective transmission of UV light and bacteria fluorescing light to an area infected with bacteria or other pathogens. The device 50 is provided with self-contained power supply 51, in handle housing 52 (a power line for additional power may also be attached to the handle), which powers UV pathogen-disrupting emitted light from UV LED 57. The UV light is transmitted and directed through a transmission medium of a collimating lens 56 and beam splitter 55 to speculum 58, which is aimed at the bacteria or other pathogen infected site.

The otoscope 50 configuration includes the ability to snap on removable specula-type adapters 58 that may include further optics such as lenses, fibers or light pipes, to gain further access into inaccessible or difficult to reach areas, such as the Eustachian tube, trachea, sinuses, surgical openings and wounds, including access openings for disinfection of implanted devices.

Reduced conical section 59 has external distal white LEDs 59*a* for illumination of the target site. CCD camera chip 53*a* receives the image of the aimed area and transmits it for viewing on screen 53. UV light 190 emitted from conical section 59 bathes the viewing site with UV disrupting light for killing pathogens in the viewed area. As shown in FIGS. 6C and 6D, light of a wavelength such as 405 nm fluoresces bacteria 64 of surgical site 62 and the otoscope device includes an LED 57*a* which emits such light on demand whereby the user can see the fluoresced bacteria 64 on viewing screen 61 and can move the aim of the otoscope device 50 to direct such fluorescing light and UV light for facilitated pathogen eradication at bacteria infected sites 64. Alternatively, the source of the fluorescing light which which may comprises several sources (with differing waves lengths which fluoresce different bacteria) may be incorporated in the ring 59*a* together with the white light illumination LEDs The target sites include sore throats in mouths or surgical operation sites 62 as shown in FIG. 6B. Trained collimated UV light from devices such as the otoscope like device 50, when used before, during and after surgery markedly reduces even the most disinfectant resistant bacteria from the site with removal of MRSA and reduction, if not elimination, of SSI. Though shown as handheld in FIG. 6B, the device can be supported on a movement-controlled stand (out of the way of the surgical procedure) and may even be automatically guided by feedback supplied by fluorescing of bacteria for the application thereto of UV light 190. Though the UV light is shown as being offset from the generating LED by 90° it can be more directly applied with rearrangement of the light source in the device to directly output the UV light from a transmitting lens directly through output section 59.

FIG. 6E depicts a currently utilized nasendoscope configuration 50' fitted with a UV carrying fiber 18*c* (and self-contained UV light source and power supply—not shown) for effecting bacteria disinfection in areas requiring fiber extensions for being reached such as inner ear 150 with ear infection, through Eustachian tube 151.

FIG. 7 shows a cross section view of an implanted pacemaker 71 in a human with a UV optical fiber 180 used to disinfect the pacemaker in situ. FIG. 7A shows the disinfection procedure in a cross-section view of the implanted pacemaker into pocket 74 between outer skin 72 and muscle layer 73. UV carrying fiber 180 is inserted into a skin incision adjacent the pacemaker and then moved across the surfaces 71*a* of the pacemaker to effect disinfection in situ without the need for surgical removal and attendant complications. To facilitate disinfection and since the fiber is inserted laparoscopically rather than through an endoscope, the fiber may be provided with a broadened UV light dispersing end which can also serve as a wedge to separate the surrounding skin from the pacemaker surfaces. Other implanted devices may be similarly disinfected in situ.

FIGS. 8 and 8A illustrate an additional embodiment used with endoscope biopsy channels, particularly with endoscopes which have not been immediately sterilized and a bio film has started to form over pathogens contained within the biopsy channel. This bio-film may retard the effect of UV light on the pathogens by limiting penetration. A combination wire with integrated absorbent material 80 serves to disrupt the bio-film and any UV light blocking characteristics. The relatively stiff wire element 81, with spongy absorbent section 82 (similar to a dental floss type configuration) of the combination 80 is inserted into the biopsy channel 20 prior to insertion of a UV light emitting fiber, as shown in FIG. 8A. The absorbent section 82 expands radially in the direction of the arrows, with full engagement with the channel walls 20*a* and biofilm 83. The absorbent section material 82 disrupts any biofilm by absorption and physical engagement particularly when the absorbent section 82 is moved by retraction of the wire support 81 and removal of the combination from the biopsy channel.

The chart in the flow chart of FIG. 9 illustrates that light (including UV light) is normally blocked from passing through tissue 91 as a result of the presence in the tissue of light scattering lipids and light absorption pigments. Refractive index matching with dissociation of collagen, delipidation, decalcification, dehydration and hyperhydration serve to lower the light scattering effect within tissues and cells. Pigment removal with decolorization serves to reduce light absorption within the tissues and cells to the extent that the tissues become essentially transparent with the tissue clearing. This has been done in vivo for direct observation of biological processes within animals and some work with humans.

As illustrated in FIG. 10 UV light treatment of pancreatic cancer shown on pancreas 110 as tumors 111 and 112 is facilitated with initial tissue clearing of the tumors with clearing chemicals being inserted into the tumors by aspiration needles 118 with access to the tumors through the duodenum 113 adjacent the pancreas. The tumors are rendered more transparent to light whereby UV light subsequently provided to the tumors with the aspiration needles has an effective increase of penetration from about 40 microns to at least one to several millimeters whereby the UV light provides an effective non traumatic tumor killing expedient not previously available. This procedure is effective as against any cancer since they all contain DNA/RNA which is disrupted by UV light. While a needle or similar device is used for delivery of chemicals for tissue clearing, the fiber itself, as well as the needle, may be used for penetration into the cancer tissues for direct delivery of the cancer disrupting LV light.

FIG. 9B shows a prior art, Sung, K. et al. *Simplified three-dimensional tissue clearing and incorporation of colorimetric phenotyping*. Sci. Rep. 6, 30736; doi: 10.1038/srep30736 (2016), tissue clearing of a mouse brain 92 from the opaque to translucent 92*a* (12 days) to completely transparent 92*b* (19 days), wherein markings 94 on a base support 93 are visible therethrough. FIG. 9C shows a similar prior art tissue clearing of a human basal tumor 96 from opaque to translucent/transparent 96*a* (21 days). These studies thus validate tissue clearing in tumors of humans whereby UV light has extended depth of penetration of at least a millimeter to full tumor penetration and UV light treatment of all cancer cells in a tumor without trauma such as with x-ray or gamma radiation. In addition, tumor size is controllable without trauma and possibly to the extent of even stage 4 cancer treatment.

It is understood the procedures described in FIGS. 3-5C may be used in combination with the tissue clearing procedures in order to facilitate operation with increased UV light depth of penetration.

Judicious mapping of the tumor with controlled administration of tissue clearing chemicals effectively confines the chemical effect of tissue clearing to the tumor and some surrounding tissue (to ensure complete cancer tumor eradication). Tissue clearing is not a significant toxic procedure per se, particularly when so confined, and restoration of lipids and pigments to cleared tissues are also believed to occur over time. Confinement of the tissue clearing to a tumor (and surrounding tissue) is also an automatic barrier for prevention of spreading of tissue necrosis by the applied UV light to areas surrounding the tumor which have not been cleared because of the lack of significant depth of penetration in such areas.

FIGS. 10A-D illustrate various embodiments wherein UV light may be utilized for rapidly sterilizing the exterior of endoscopes or other similar medical instruments. Though, as described above, full endoscope disinfection with UV light has been eschewed because of fears of endoscope polymer breakdown by the UV light, the apparatus embodiments of FIG. 10A allow for very rapid sterilization before the UV used in the sterilization has time to affect polymers (DNA/RNA disruption in pathogens by UV is much more rapid than breakdown of polymeric bonds). FIG. 10A shows an endoscope 120 with operational handle section 120*b* of a first diameter and the insertion tube 120*a* of a lesser diameter enclosed and position locked within a transparent protective enclosure 121 having a larger diameter 121 and a smaller diameter 122.

Figure 10B:
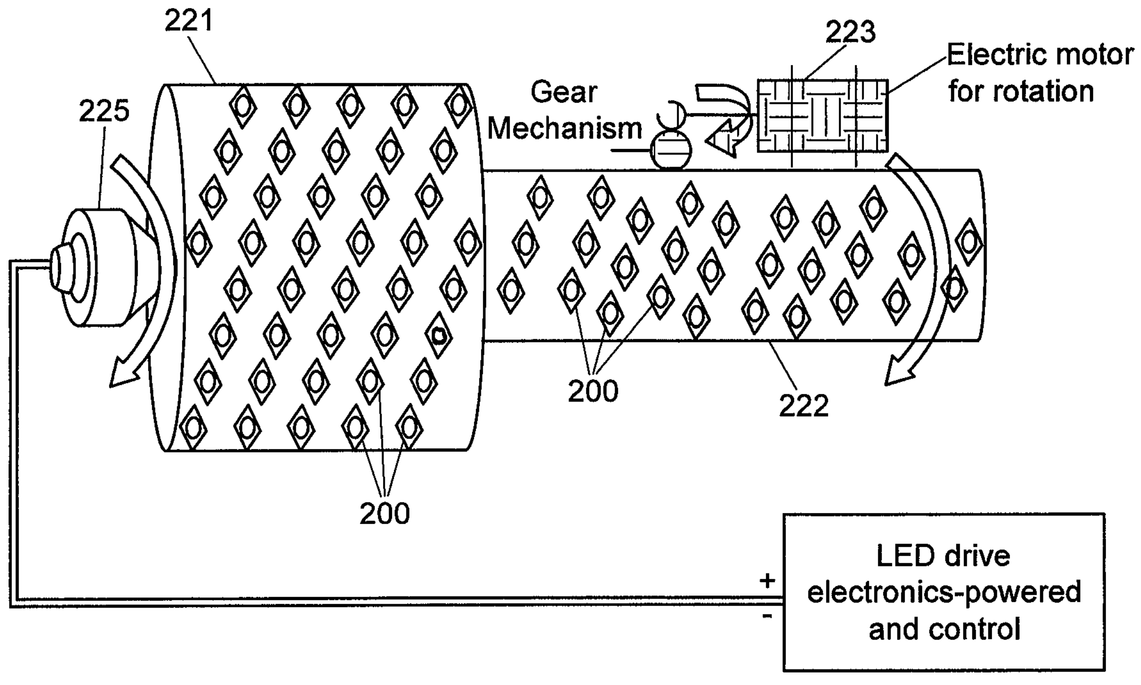

The endoscope 120, as enclosed in protective enclosure 121, is fitted into a larger corresponding structure 221 and 222 shown in FIG. 10B with the structure 221 having an array of UV emitting LEDs on the inner surface thereof. The protective enclosure 121 is engaged with rotating element 225 powered by motor 223. The endoscope 120 is thereby completely bathed in UV (passing through protective enclosure 121) from a close distance and when calculated full sanitization is effected, the LEDs are turned off and the protective enclosure is removed from structure 221 and the endoscope is removed the protective enclosure 121. The UV light exposure time, depending on the power of the LEDs, of the endoscope can be as little as several seconds to several minutes, well under any time for the affecting of the polymeric components of the endoscope by the UV light. Automatic control time for LED activation with rotation ensures that the endoscope is not expose to UV light for any excess time above that need for sanitization.

FIGS. 10C and 10D depict another automated method for sterilization of an endoscope with UV light. In FIG. 10C endoscope 120 with small diameter insertion tube 120*a* and larger diameter handle 120*b* is suspended by hook 120'. Track element 126 has a track groove 127 of length A equal to or greater than the insertion tube 120*a*. Movable track element 129 controllably moves up and down the length of track groove 127 and has handle section 128 and small ring 128*a* (sized to closely accommodate but not touch insertion tube 120*a*) with UV LEDs distributed around the inner circumference thereof. In use, the track groove 127 is aligned with insertion tube 120*a* and the insertion tube is inserted within ring 128*a*. The LEDs in ring 128*a* are activated and the ring 128*a* is either manually moved with handle 128 or mechanically moved with movement of track element 129 along the length of the track groove 127 whereby every portion of insertion tube 120*a* is bathed with UV light for a sufficient time for the sanitization thereof.

FIG. 10D shows a similar track element 126*a* with track groove 127*a* of length B (the same as or larger than handle section 120*b* of the endoscope) with track element 129*a*, handle section 128' and larger ring 128'*a* sized to accommodate the greater diameter of handle 120B. The handle 120*b* of the endoscope 120 is similarly sanitized as with the procedure used with the insertion tube. Time of UV exposure should be limited to that required for sanitization and not much more to avoid any effect on polymeric integrity FIGS. 11A and 11B illustrate an example of a manufacturing procedure requiring sanitization of large amounts of items such as laboratory pipettes, syringes or catheters (generally all of cylindrical configuration), FIG. 11A depicts an array of manufactured pipettes 131 in a processing case 130 with their respective open ends facing upward. Conveyor sanitization station 135 in FIG. 11B shows a linear placement of numerous cases 130 with arrays of pipettes as shown in FIG. 11A where the pipette cases are arranged on an assembly line in a uniform bulk configuration. At the station position shown, mass sanitization element 136 is movably positioned on track 137. Sanitization element 136 contains downwardly extending short UV transmission fibers 138 in an array and relative position and number corresponding to the pipettes in cases 130. The sanitization element 136 is moved and stopped into alignment position successively with the pipettes 131 in cases 130. The array of aligned UV transmitting short fibers are lowered en masse and inserted into the aligned pipettes 131 and UV light is transmitted from the fibers into each of the aligned pipettes for a time sufficient to effect sanitization. The fibers are withdrawn for a next batch to be sanitized with the sanitization element being moved to the next case for the same sanitization with the process being continuous, rapid and economical without need for chemicals or washing in a reliable sanitization procedure.

An automated and data controlled biopsy channel disinfection apparatus is shown, with a disinfection protocol, in FIGS. 12A-B. As a first step, in FIG. 12A, the distal end 18" of a UV emitting fiber 18 is tested for amount of emitting UV power by insertion into an output measuring device, integrating sphere 145 which collects power impinging on wall 148 and collection output measurement to detector 147. An alternative UV emitting laser apparatus 10 as shown in FIG. 1A has an integrated power output measuring meter positioned to measure UV power output 9*a*.

The output power from either the detector 147 in FIG. 12A or the power measuring meter in FIG. 1A is provided to a computer (not shown) which is also provided with the factors of fiber diameter and inner diameter of the biopsy channel for a determination of distance between the fiber and biopsy walls to be disinfected. Tables of pathogens with individual pathogen requirements for DNA/RNA disruption are contained in a database of the computer which calculates appropriate position dwell time for effective disinfection (with additional safety margin). The computer output is sent to timer 141 and retraction device 140 in FIG. 12B via input 143 for control of fiber retraction time by retraction device 140. The UV emitting fiber 18 is fully inserted into the biopsy channel 120 in FIG. 12B, connected to puller element 142 and retraction device 140 is activated to retract the fiber 18 while UV light is continuously passing through fiber 18 and out the distal end thereof with UV light 19 sanitizing the walls of the biopsy channel with continuous position UV emission and dwell time conforming to the calculated value for full disinfection. The retraction device may either be linear (with a length greater than the length of the biopsy channel on fiber guiding bed 246) such as with a relatively non-flexible fiber or spool shaped, with a flexible fiber. The process may be a single step one, or it may be repeated for greater certainty in disinfection if necessary. In any event, disinfection times are generally from about one to five minutes depending upon ascertained values of UV power and application distances. With the automation and computer control, human error and inconsistencies are minimized to ensure a more reliable disinfection especially since visual control is not directly possible. It is understood that disinfection times with UV light application are extended to include a safety buffer time period to ensure that disinfection is complete regardless of the nature of the pathogen being eradicated.

The fiber 18 may also be provided with an RFID device or the like to verify that the fiber is a genuine one with proper UV solarization resistance and UV transmission capability. The RFID device may also be configured to keep track of the number of times that the fiber has been used to transmit UV light with an operational cutoff at a predetermined point of unacceptable fiber degradation FIGS. 13A and 13B illustrate the use of an endoscope 120 to carry an aspiration needle 153 to a cancer site tumor 151 on lymph node 152 with the needle 153 (used in the prior art to carry ultrasound instruments for mapping and therapeutic treatment of tumors EBUS and TEBUS) to carry a UV emitting fiber to the tumor and also solvents for rendering the tumor transparent. As shown, the endoscope 120 is inserted into the esophagus 154 of the patient and the insertion tube 121*a* of the endoscope is brought into a position wherein the needle 153 is carried into proximity to the cancer site 151. As shown in the expanded view of FIG. 13B, elevator 123 of the biopsy channel within insertion tube 121*a* controls placement of the needle 153 relative to the tumor 151. Control of the needle 153 is independent of control of the fiber 18 contained therein (shown in FIG. 13C) whereby the needle 153 with contained fiber 18 is inserted into the tumor 151 and the needle 153 is retracted to leave the UV emitting distal end of fiber 18 imbedded within the tumor 151. UV light transmitted through the fiber 18 as light 19 effective kills the pathogenic (as defined) cancer cells from within the tumor, without significant effect on healthy cells.

It is understood that the above descriptions and examples of the invention are merely illustrative and that changes may be made to components and procedures without departing from the scope of the following claims.

What is claimed is:

1. A method for enhancing the pathogenic eradication effect of UV light of a wavelength between 200 nm to 340 nm on a pathogen infected area within or on a human or animal, wherein pathogens are defined as being selected from bacteria, viruses, cancer, noxious cells, tissue, and micro-organisms and healthy cells, which may become toxic, the method comprising at least one of the steps of:

a. placing the UV light with directed transmission of the UV light onto a surgical site of the human or animal before, and optionally during and after a surgical procedure with sufficient power to maintain a substantially pathogen free environment during time of the surgical procedure;

b. directing transmitted UV light with sufficient power over a reasonable period of time through and onto a pathogen infected area adjacent an orifice within a human or animal to for deactivation of pathogens in infected the area;

c. rendering a cancer infected site within or on the human or animal increasingly susceptible to significant UV light penetration with cancer inactivation thereof; or isolating a cancer infected site from spreading by at least one of:

i. rendering the cancerous site more transmissive to UV light penetration;

ii. utilizing UV light pathogen eradication to form an inactiactivater cancer barrier between the cancer infected site and a non-cancer infected site; and iii. rendering the cancer infected site more susceptible to the significant UV light penetration with the repeated steps of cancer deactivation of infected areas with UV light and removal of the cancer deactivated areas to expose additional cancer infected sites to the UV light, d. bathing a cancer infected site with UV light after cancer cells have been removed from the infected site to increase extent of remission with recurrence of cancer infection; and e. disinfecting outer surface areas of an implanted device in a human or animal in situ within the human or animal, with UV light, without removing the implanted device from the human or animal, by deploying UV light of sufficient power disinfection of pathogens, for a reasonable period of time, on outer surface areas of the implanted device.

2. The method of claim 1, wherein the UV light source is a UV light emitting laser with relatively high UV light output power sufficient to provide pathogen deactivation power along substantially the entire length of a side emitting optical fiber optically aligned and attached to the output of the laser.

3. The method of claim 1, wherein a hand-held device is configured to provide pathogen deactivating UV light from a distance from a pathogen infected site.

4. The method of claim 1, wherein the pathogen infected site is tissue which is cleared to render it more transmissive to UV light penetration.

5. The method of claim 1, wherein direct transmission or directed transmitted UV light is through a collimated lens which provides the sufficient power, over a reasonable period of time, to maintain the substantially pathogen free environment or to disinfect the area.

6. The method of claim 1, wherein a pathogen infected site or area or a surgical site is bathed with a wavelength light which causes pathogens to fluoresce to provide a target for the UV light pathogen inactivation.

7. The method of claim 1, wherein the pathogens, which are inactivated, and cells, comprising the pathogen infected areas which are killed by the UV light, are removed by suction or washing.

8. The method of claim 1, wherein UV light is transmitted and carried into a human or animal through an optical fiber movably fitted within a hollow needle of a dimension capable of puncturing into a site within the human or animal with minimal harm.

9. The method of claim 1, wherein the implanted device comprises a pacemaker and wherein the deployment of the UV light is in a pocket used for implantation of the pacemaker within the human or animal.

* * * * *